United States Patent
Matos-Perez et al.

(10) Patent No.: US 10,304,720 B2
(45) Date of Patent: May 28, 2019

(54) LASER ABLATIVE DIELECTRIC MATERIAL

(71) Applicant: Brewer Science Inc., Rolla, MO (US)

(72) Inventors: Christina R. Matos-Perez, Rolla, MO (US); Tony D. Flaim, St. James, MO (US); Arthur O. Southard, St. James, MO (US); Lisa M. Kirchner, Rolla, MO (US); Deborah Blumenshine, St. James, MO (US)

(73) Assignee: Brewer Science, Inc., Rolla, MO (US)

( * ) Notice: Subject to any disclaimer, the term of this patent is extended or adjusted under 35 U.S.C. 154(b) by 0 days.

(21) Appl. No.: 15/650,535

(22) Filed: Jul. 14, 2017

(65) Prior Publication Data
US 2018/0019156 A1 Jan. 18, 2018

Related U.S. Application Data

(60) Provisional application No. 62/362,674, filed on Jul. 15, 2016, provisional application No. 62/404,803, filed on Oct. 6, 2016.

(51) Int. Cl.
*H01L 21/762* (2006.01)
*B41C 1/10* (2006.01)
(Continued)

(52) U.S. Cl.
CPC .......... *H01L 21/762* (2013.01); *B41C 1/1033* (2013.01); *C07C 65/21* (2013.01);
(Continued)

(58) Field of Classification Search
CPC ..................................................... H01L 21/762
See application file for complete search history.

(56) References Cited

U.S. PATENT DOCUMENTS 3,124,559 A   3/1964  De Witt
3,182,039 A   5/1965  Remy
(Continued)

FOREIGN PATENT DOCUMENTS

KR   10-2016-0029097   3/2016
WO        96/27212       9/1996
WO        2004/003044    1/2004

OTHER PUBLICATIONS

Hirose et al., "Synthesis and Thermal Analysis of Polyacylhydrazones Having Guaiacyl Units with Alkylene Groups," Sen-I Gakkaishi, Jul. 13, 1983, vol. 39, No. 11, pp. 496-500.
(Continued)

*Primary Examiner* — Thao P Le
(74) *Attorney, Agent, or Firm* — Hovey Williams LLP

(57) ABSTRACT

Dielectric materials with optimal mechanical properties for use in laser ablation patterning are proposed. These materials include a polymer selected from the group consisting of polyureas, polyurethane, and polyacylhydrazones. New methods to prepare suitable polyacylhydrazones are also provided. Those methods involve mild conditions and result in a soluble polymer that is stable at room temperature and can be incorporated into formulations that can be coated onto microelectronic substrates. The dielectric materials exhibit high elongation, low CTE, low cure temperature, and leave little to no debris post-ablation.

18 Claims, 18 Drawing Sheets

(51) Int. Cl.
  *C07C 65/21*    (2006.01)
  *C07C 65/30*    (2006.01)
  *C07C 243/12*   (2006.01)
  *C08G 69/38*    (2006.01)
  *C08G 18/76*    (2006.01)
  *C08G 12/06*    (2006.01)
  *C08G 73/02*    (2006.01)
  *C08G 18/38*    (2006.01)

(52) U.S. Cl.
  CPC ............ *C07C 65/30* (2013.01); *C07C 243/12* (2013.01); *C08G 12/06* (2013.01); *C08G 18/3872* (2013.01); *C08G 18/7671* (2013.01); *C08G 69/38* (2013.01); *C08G 73/02* (2013.01)

(56) References Cited

U.S. PATENT DOCUMENTS

| | | | |
|---|---|---|---|
| 3,198,767 A | 8/1965 | Matsuda et al. | |
| 3,354,122 A | 11/1967 | Michel | |
| 4,316,967 A * | 2/1982 | Hergenrother | C08C 19/44 |
| | | | 521/134 |
| 5,766,497 A | 6/1998 | Mitwalsky et al. | |
| 5,785,787 A | 7/1998 | Wojnarowski et al. | |
| 6,080,526 A | 6/2000 | Yang et al. | |
| 6,255,718 B1 | 7/2001 | Janai et al. | |
| 7,453,148 B2 | 11/2008 | Yang et al. | |
| 7,632,753 B1 | 12/2009 | Rusli et al. | |
| 8,557,683 B2 | 10/2013 | Lei et al. | |
| 2002/0123134 A1 * | 9/2002 | Huang | B01J 19/0046 |
| | | | 435/287.2 |
| 2006/0271032 A1 * | 11/2006 | Chin | A61B 18/1482 |
| | | | 606/41 |
| 2007/0172583 A1 * | 7/2007 | Lin | C23C 24/08 |
| | | | 427/126.3 |
| 2008/0052904 A1 | 3/2008 | Schneider et al. | |
| 2010/0210745 A1 * | 8/2010 | McDaniel | C09D 5/008 |
| | | | 521/55 |
| 2011/0028815 A1 * | 2/2011 | Simpson | A61B 5/14532 |
| | | | 600/345 |
| 2015/0011073 A1 * | 1/2015 | Lei | H01L 21/78 |
| | | | 438/462 |
| 2015/0065020 A1 * | 3/2015 | Roy | B24B 37/26 |
| | | | 451/529 |
| 2015/0207023 A1 * | 7/2015 | Nielson | H01L 31/1876 |
| | | | 438/68 |
| 2017/0038510 A1 * | 2/2017 | Sudeji | B29D 11/0073 |

OTHER PUBLICATIONS

Skene et al., "Dynamers: Polyacylhydrazone reversible covalent polymers, component exchange, and constitutional diversity," PNAS, Jun. 1, 2004, vol. 101, No. 22, 8270-8275.

Labib et al., "Copper(II) and nickel(II) metallopolymers derived from polyacylhydrazones," Transition Metal Chemistry, Dec. 2000, vol. 25, Issue 6, pp. 700-705.

Jarraya et al., "New polyacylhydrazone dynamers incorporating furan moieties," Mediterranean Journal of Chemistry, 2014, 2(6), 708-718.

Correia et al., "Selective Laser Ablation of Dielectric Layers," 22nd EU PVSEC, 2007, 7 pages.

Thorstensen et al., "New approach for the ablation of dielectrics from silicon using long wavelength lasers," Energy Procedia 38 (2013) 787-793.

Hubbard, Robert L., "New Material and Reliability Issues of Re-Distribution Layers," Proc 4th In. Wafer Level Packaging Conf, San Jose, CA, Sep. 2007, 4 pages.

"Pulsed laser ablation improves holographic lens fabrication," Jan. 15, 2016, posted by Gail Overton, Senior Editor, 3 pages, vww.laserfocusworld.

International Search Report and Written Opinion dated Oct. 26, 2017 in corresponding PCT/US2017/042225 filed Jul. 14, 2017.

Ono et al., "Dynamic polymer blends—component recombination between neat dynamic covalent polymers at room temperature," Chem. Commun., 2005, 1522-1524.

* cited by examiner

US 10,304,720 B2

LASER ABLATIVE DIELECTRIC MATERIAL

RELATED APPLICATIONS

This application claims the benefit of U.S. Provisional Application Nos. 62/362,674, filed Jul. 15, 2016, and entitled SOLVENT-SOLUBLE POLYACYLHYDRAZONES USEFUL FOR MICROELECTRONIC COATING APPLICATIONS, and 62/404,803, filed Oct. 6, 2016, and entitled LASER ABLATIVE DIELECTRIC MATERIAL, each of which is incorporated by reference herein.

BACKGROUND OF THE INVENTION

Field of the Invention

This invention relates to dielectric materials suitable for laser ablation, as well as novel polymers that can be used to form those dielectric materials.

Description of the Prior Art

Laser ablation of dielectric materials allows the use of diverse chemistries and reduces the number of steps and processing time required compared to traditional lithographic processes. Mechanical properties such as high elongation, low coefficient of thermal expansion (CTE), and low cure temperatures are key to obtaining a robust dielectric platform. Currently, there is not a dielectric material available where the properties and low debris formation are tailored for this application.

SUMMARY OF THE INVENTION

In one embodiment, the invention provides a method of patterning a dielectric layer supported on a substrate. The method comprises ablating the dielectric layer by exposing it to laser energy so as to facilitate ablation of at least a portion of the dielectric layer. The improvement is that the dielectric layer is formed from a composition comprising a polymer selected from the group consisting of polyureas, polyurethanes, and polyacylhydrazones.

In another embodiment, the invention provides a structure comprising a microelectronic substrate and a dielectric layer on the substrate. The substrate is selected from the group consisting of silicon, SiGe, $SiO_2$, $Si_3N_4$, SiON, aluminum, tungsten, tungsten silicide, gallium arsenide, germanium, tantalum, tantalum nitride, $Ti_3N_4$, hafnium, $HfO_2$, ruthenium, indium phosphide, coral, black diamond, and glass substrates. The dielectric layer is formed from a composition comprising a polymer selected from the group consisting of polyureas, polyurethanes, and polyacylhydrazones. Additionally, the dielectric layer has an upper surface and a lower surface, with the upper surface being remote from the microelectronic substrate and the lower surface being adjacent the microelectronic substrate. The dielectric layer also comprises at least one opening formed therein. The at least one opening has an upper edge at the upper surface, and there is laser ablation residue from the polymer at, near, or both at and near that upper edge.

In a further embodiment, the invention provides a method of forming a polyacylhydrazone where the method comprises reacting a dihydrazide with a 2-hydroxyalkyl-linked dialdehyde to form the polyacylhydrazone. The alkyl of the 2-hydroxyalkyl-linked dialdehyde has an odd number of carbon atoms.

In yet a further embodiment, the invention is directed towards a polyacylhydrazone comprising recurring monomers of a dihydrazide and a 2-hydroxyalkyl-linked dialdehyde, where the alkyl of the 2-hydroxyalkyl-linked dialdehyde has an odd number of carbon atoms. The polyacylhydrazone has a solubility of at least about 10% by weight in a polar, aprotic solvent.

DETAILED DESCRIPTION OF THE PREFERRED EMBODIMENTS

Figure 1:
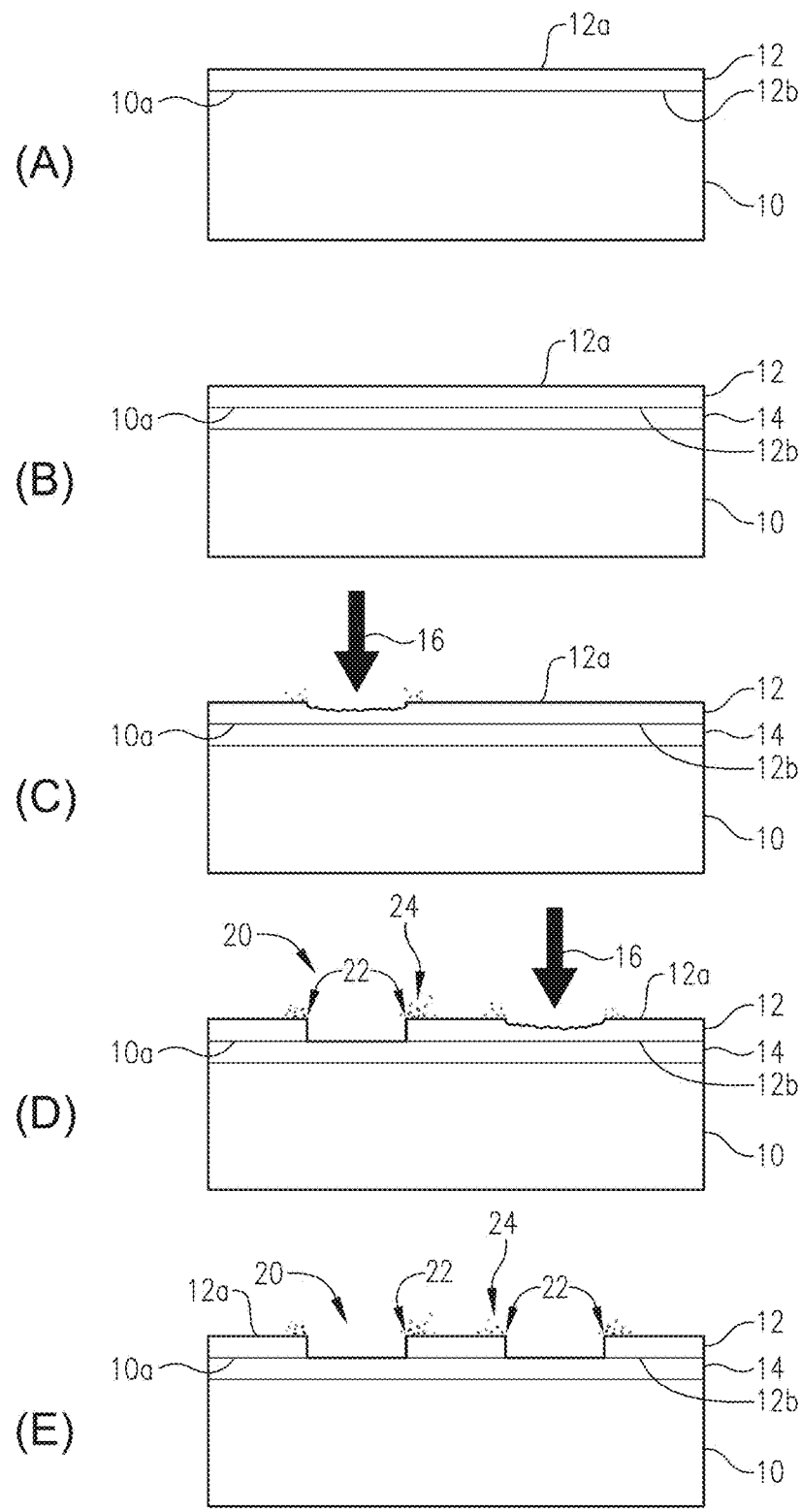
FIG. 1 is a schematic drawing depicting a structure (not to scale) formed by the inventive compositions and process.

Materials and processes for laser ablation are broadly provided. The material comprises a copolymer made of two or more monomers dissolved in a solvent system.

Polymers for Use in Inventive Materials

1. Polyureas and Polyurethanes

In one embodiment, the polymer is selected from the group consisting of polyureas, polyurethanes, and combinations thereof. More preferably, the polymer is selected from the group consisting of polyurea sulfones, polyurethane sulfones, and combinations thereof.

A particularly preferred polyurea sulfone includes recurring diisocyanate monomers and monomers selected from the group consisting of amine-terminated sulfones, hydroxyl-terminated sulfones, and mixtures thereof. The diisocyanate monomer can be any difunctional isocyanate with preferred such monomers being selected from the group consisting of isophorone diisocyanates, toluene-2,4-diisocyanates, aromatic or aliphatic diisocyanates, and combinations thereof. Two especially preferred monomers are:

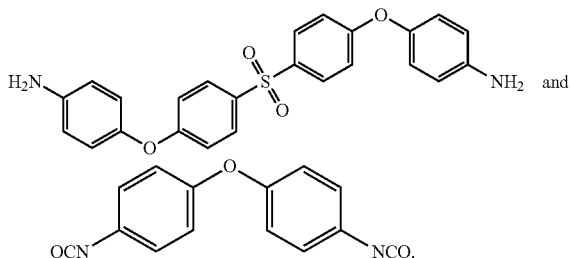 and

These polymers can be formed by mixing the desired monomers with a solvent system at room temperature. The molar ratio of the first monomer to the second monomer is preferably from about 0.95:1.00 to about 1.05:1.00, and more preferably from about 1.00:1.00. Preferably, the monomers comprise from about 60% by weight to about 90% by weight of the polymerization mixture, as taken as a percent of the mixture as a whole. It will be appreciated that the quantities of monomers used depends upon the amount of solvent and additional components used.

Suitable solvents for the polymerization reaction include those selected from the group consisting of cyclopentanone, cyclohexanone, dimethylformamide (DMF), dimethylsulfoxide (DMSO), N,N-demthylacetamide (DMAC), gamma butyrolactone (GBL), and mixtures thereof. The solvent is present in the reaction mixture at levels of from about 10% by weight to about 40% by weight, as taken as a percent of the polymerization mixture as a whole. The amount of solvent used depends upon the amount of the monomers and additional components used.

The polymerization is typically completed in a time period of from about 4 hours to about 24 hours, depending upon the amount of monomers used. Optionally, additional components may be added to the polymerization reaction, including those selected from the group consisting of endcappers, catalysts, initiators, and mixtures thereof. Endcappers may be included to prevent further polymerization, and preferably include an amine or hydroxyl-terminated compound. Additional components can comprise from about 1% by weight to about 20% by weight of the reaction mixture, depending on the quantities of monomers, solvent, and the additional component(s) used.

2. Polyacylhydrazones

In another embodiment, the polymer can be a polyacylhydrazone. Preferred polyacylhydrazones include recurring dihydrazide monomers and recurring dialdehydes. Particularly preferred dihydrazides include those selected from the group consisting of adipic acid dihydrazide (ADH), isophthalic acid dihydrazide (IDH), and combinations thereof. Preferred dialdehyde monomers are 2-hydroxyalkyl-linked dialdehydes, where the alkyl is preferably one with an odd number of carbon atoms (e.g., $C_1$, $C_3$, $C_5$, $C_7$, etc.). Particularly preferred dialdehyde monomers are 2-hydroxypropyl-linked dialdehydes, and even more preferably 2-hydroxypropyl-linked aromatic dialdehyde. One such preferred monomer is:

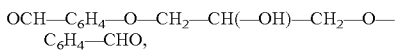

where [—$C_6H_4$—] represents a six-membered aromatic ring structure, and both of the ether linking groups attached to the aromatic rings reside either in the para position or the meta position relative to the formyl substituents on their respective rings. Some especially preferred monomers include 1,3-bis(4-formylphenoxy)-2-hydroxypropane (where the ether linking group is para to the formyl group), 1,3-bis(3-formylphenoxy)-2-hydroxypropane (where the ether linking group is meta to the formyl group, 1,3-bis(4-formyl-2-methoxyphenoxy)-2-hydroxypropane, 1,3-bis(3-formyl-2-methoxyphenoxy)-2-hydroxypropane, and 1,3-bis(4-formyl-2-ethoxyphenoxy)-2-hydroxypropane.

The dialdehydes can be obtained commercially, or they can be prepared in high yields by reacting a hydroxybenzaldehyde compound with epichlorohydrin in a solvent in the presence of a strong base such as sodium, potassium, or tetramethylammonium hydroxide (TMAH) in an aqueous alcohol solution. TMAH is particularly preferred for preparing ingredients that will be used in microelectronic coating products because it is does not contribute unwanted metal ion contamination.

A wide range of hydroxybenzaldehyde compounds can be used to prepare 2-hydroxypropyl-linked aromatic dialdehydes (the most preferred dialdehyde monomer). However, commonly available reagents such as 3- and 4-hydroxybenzaldehyde are preferred as they impart superior solubility, thermal, and mechanical properties to the final polyacylhydrazone structure.

Suitable solvents include those that do not hydrolyze or create byproducts in a basic environment. Preferred solvents include low-boiling-point alcohols such as those selected from the group consisting of methanol, ethanol, and isopropanol. These solvents are preferred for maintaining a constant reaction temperature by holding the reaction mixture at its reflux point. The solvent should be present in the reaction solution at levels of from about 40% by weight to about 80% by weight, and preferably from about 50% to about 70% by weight, based upon the total weight of the reaction solution taken as 100% by weight.

The reaction is carried out at a temperature of from about 60° C. to about 120° C., and preferably from about 80° C. to about 100° C., for a time of from about 4 hours to about 24 hours, and preferably from about 6 hours to about 12 hours. The dialdehyde products crystallize cleanly and in high yield when the reaction mixture is cooled to room temperature or below.

In a further embodiment, substituted dialdehydes may be used. Suitable substituted dialdehydes include those in which a substituent X is attached to the aromatic ring in one of the positions that would otherwise be occupied by hydrogen. Preferred substituent X groups include those selected from the group consisting of —R, —OR, or halogens (e.g., —Cl), where R is selected from the group consisting of alkyl moieties (e.g., methyl, ethyl, propyl, butyl).

In one embodiment, terephthalaldehyde may be used as a comonomer with the dialdehyde monomer. However, in such instances, the molar ratio of terephthalaldehyde to the dialdehyde monomer will preferably not exceed about 1:3.

The polyacylhydrazones are formed by condensing the dihydrazide and dialdehyde monomers in a solvent, preferably a polar, aprotic solvent. Suitable such solvents include those selected from the group consisting of dimethyl sulfoxide, N,N-dimethylformamide, N,N-dimethylacetamide, N-methylpyrrolidinone, and mixtures thereof. The solvent is preferably present at levels of from about 60% by weight to about 90% by weight, and preferably from about 75% by weight to about 90% by weight, based upon the total weight of the polymerization reaction mixture taken as 100% by weight. Additional solvent may be added to the reaction mixture during polymerization to maintain a manageable viscosity of the solution. The molar ratio of the dihydrazide monomer to the dialdehyde monomer is preferably from about 0.95:1.00 to about 1.05:1.00, and more preferably from about 1.00:1.00. Both monomers are present in the composition at levels of from about 5% to about 15% by weight, and preferably about 9% by weight, based upon the total weight of the polymerization reaction mixture taken as 100% by weight.

The polymerization reaction does not require a catalyst, and in one embodiment the reaction is carried out essentially free (i.e., less than about 0.001% by weight, and preferably about 0% by weight) of a catalyst. In another embodiment, the polymerization reaction may be accelerated by the addition of a small amount of acid. Suitable acids include those selected from the group consisting of acetic acid, trifluoroacetic acid, sulfuric acid, and hydrochloric acid. The acid is present in the material at levels of from about 1 mole % to about 5 mole %, based on the combined molar quantity of the dihydrazide and dialdehyde monomers, and preferably from about 2 mole % to about 3 mole %, based on the combined molar quantity of the dihydrazide and dialdehyde monomers.

Advantageously the resulting polyacylhydrazones of the present invention are more amorphous than prior art polyacylhydrazones, making them more soluble than prior art polyacylhydrazones. That is, the inventive polyacylhydrazones have a solubility of at least about 10% by weight in a polar, aprotic solvent (e.g., dimethyl sulfoxide, N,N-dimethylformamide, N,N-dimethylacetamide, N-methylpyrrolidinone, and mixtures thereof). As used herein, "polyacylhydrazone solubility" is determined by the formation of a clear, precipitate-free solution that remains stable (i.e., doesn't fall out of solution) for at least 90 days at room temperature.

Preparation of Formulations

The formulations are prepared by mixing the particular polymer with a solvent or solvent system at room temperature for a time period of from about 2 hours to about 12 hours, and preferably from about 4 hours to about 8 hours.

In the final inventive formulation, the polymer is present at levels of from about 10% by weight to about 40% by weight, and preferably from about 20% to about 30% by weight, based upon the total weight of the final composition taken as 100% by weight. The solvent system is present at levels of from about 60% by weight to about 90% by weight, and preferably from about 70% to about 80% by weight, based upon the total weight of the composition taken as 100% by weight. It will be appreciated that the amount of solvent or solvents added to the material may be different, depending on the deposition method utilized.

Suitable solvents for the final formulation include those selected from the group consisting of cylcopentanone, cyclohexanone, dimethylformamide, gamma butyrolactone, dimethylsulfoxide, N,N-dimethylformamide, N,N-dimethylacetamide, N-methylpyrrolidinone, and mixtures thereof.

Optionally, other additives may be added to the final formulation, such as those selected from the group consisting of crosslinking agents, endcappers, catalysts, initiators, surfactants, wetting agents, adhesion promoters, colorants or pigments, and/or other polymers and resins. These additives would be selected depending on the desired properties and use of the final composition and must be soluble in the solvent system and compatible with the polymer in solution. Additional components may comprise from about 1% by weight percent to about 20% by weight of the composition, depending upon the amount of monomers, solvent, and the components used.

Methods of Using Formulations

The final formulation may be deposited by spin coating, spray coating, slot-die coating, or other methods compatible with solvent-based coating formulations. These techniques may require the adjustment of the polymer solids level in the solution to obtain the desired coating thickness and uniformity without defects, for example, by diluting the solution with the principal solvent and/or adding co-solvents as long as they do not cause polymer precipitation.

FIGS. 1(A)-1(D) schematically illustrate the inventive method of forming a structure using the inventive formulations. In this method, a substrate 10 having a surface 10a is provided. Any microelectronic substrate can be used in the invention. Preferred substrates are semiconductor substrates, such as those selected from the group consisting of silicon, SiGe, $SiO_2$, $Si_3N_4$, SiON, aluminum, tungsten, tungsten silicide, gallium arsenide, germanium, tantalum, tantalum nitride, $Ti_3N_4$, hafnium, $HfO_2$, ruthenium, indium phosphide, coral, black diamond, glass, and combinations of the foregoing.

The method comprises applying a quantity of the inventive composition to the substrate 10 to form a layer 12 (which is preferably an insulating dielectric layer) of the composition on the surface 10a of the substrate 10 (FIG. 1(A)). The preferred application method involves spin-coating the composition at speeds of from about 750 rpm to about 5,000 rpm (preferably from about 750 rpm to about 4,000 rpm, and more preferably from about 1,000 rpm to about 3,500 rpm) for a time period of from about 20 seconds to about 90 seconds (preferably from about 30 seconds to about 60 seconds). The substrate 10 can have a planar surface, or it can include topography features (via holes, trenches, contact holes, raised features, lines, etc.). As used herein, "topography" refers to the height or depth of a structure in or on a substrate surface. For example, the substrate 10 can comprise structure defining a hole, which includes sidewalls and a bottom wall. Thus, the method of applying the inventive composition to the substrate 10 would preferably include applying the composition to at least a portion of those hole sidewalls and bottom wall.

After the formulation is deposited, the solvent may be removed by baking at a temperature of from about 50° C. to about 250° C., preferably from about 60° C. to about 95° C., and more preferably from about 75° C. to about 90° C. The baking time used to remove the solvent may be from about 5 minutes to about 30 minutes, depending on the amount of solvent used and the baking temperature. In some embodiments, a baking step (the above baking step and/or a different baking step) can be performed to crosslink the composition in cases where a crosslinker is used.

After coating and baking, the average thickness (taken over five measurements and averaged) of the material on the substrate is preferably from about 3 microns to about 40 microns, more preferably from about 8 microns to about 20 microns, and even more preferably from about 9 microns to about 11 microns. If the substrate surface 10a includes topography, the coating 12 is preferably applied at a thickness sufficient to substantially cover the substrate topography at these thicknesses.

The layer 12 has a number of desirable properties. For example, coating or layer 12 is a dielectric layer, meaning it has a low dielectric constant. The dielectric constant of layer 12 is preferably less than about 4, more preferably from about 2 to about 4, and even more preferably from about 2.5 to about 3.5.

As noted in the figures, final coating 12 has an upper surface 12a and a lower surface 12b. Although the foregoing depicts the lower surface 12b of the dielectric layer 12 being in direct contact with the substrate surface 10(a), it will be appreciated that any number of optional intermediate layers 14 may be formed on the substrate surface 10(a) prior to processing. These intermediate layers 14 include those selected from the group consisting of adhesion promoting layers, metal layers, and both. These optional layers 14 would be formed according to conventional processes, and then the dielectric layer would be formed on top of the last/uppermost intermediate layer 14 that is utilized, following the process described above, so that the lower surface 12b of dielectric layer 12 is in contact with the uppermost intermediate layer 14. This embodiment is depicted in FIG. 1(B).

Regardless of whether intermediate layer(s) 14 are included, the dielectric layer 12 is then patterned by laser ablation, preferably using an excimer laser to expose the dielectric layer 12 to laser energy. A laser beam 16 is applied in short pulses to the material forming layer 12. The laser may be used in a "direct write" fashion in which a small laser beam is rastered only in the areas to be ablated (FIG. 1(C)), or the laser may be applied through a metal mask (not shown) so as to only ablate the areas where the laser is able to pass through the mask. The laser energy is absorbed by the material of layer 12 and as a result of various photochemical and thermal effects, portions of the layer 12 are removed to create a first opening 20 (FIG. 1(C)). The laser can then be directed to other areas of layer 12 where removal is desired and further ablation can be carried out (FIG. 1(D)) to form a further opening(s) 20 (FIG. 1(E)).

The excimer laser wavelength is preferably from about 100 nm to 850 nm, more preferably from about 150 nm to 500 nm, and even more preferably from about 200 nm to 400 nm. The pulse rate is less than about 4,000 Hz, preferably from about 1 Hz to about 4,000 Hz, more preferably from about 50 Hz to about 500 Hz, and even more preferably from about 75 Hz to about 200 Hz. The pulse length can be from about 1 ns to about 100 ns, preferably from about 3 ns to about 50 ns, and more preferably from about 5 ns to about 12 ns. The amount of material removed is dependent upon the material, laser wavelength, pulse rate, and pulse length.

There will typically be some amount of ablation debris residue (i.e., decomposed polymer) 24 that collects at and/or near the upper edge 22 of opening(s) 20 (on upper surface 12a—FIG. 1(E)). Vacuum may be applied during the ablation process to remove the ablated material to minimize or even prevent debris from forming on the surface of the dielectric. Advantageously, these materials can be ablated with minimal or substantially no debris. The amount of debris left post-ablation can be measured using optical microscopy. Ultimately, any remaining debris can be removed with an organic solvent such as cyclopentanone, cyclohexanone, dimethylformamide, dimethylsulfoxide, N,N-demthylacetamide, gamma butyrolactone, and mixtures thereof.

This selective removal can produce features such as lines of the dielectric with spaces between the lines where the dielectric material has been removed, or in vias (holes) in the dielectric material layer, and it will be appreciated that any pattern could be formed by the laser ablation. When lines and spaces are formed using the laser ablation, the width of the lines and spaces is preferably less than about 200 microns, more preferably from about 1 micron to about 70 microns, and even more preferably from about 20 microns to about to 60 microns. When vias are formed using the laser ablation, the diameter of the vias that are formed is preferably less than about 700 microns, more preferably from about 1 micron to about 500 microns, and even more preferably from about 10 microns to about 300 microns. Advantageously, the sidewalls of the features may be substantially perpendicular to the surface of the substrate, that is, the sidewalls of the features make an angle of preferably from about 70° to about 110° with the surface 10(a) of the substrate 10 (or of the surface of uppermost of any intermediate layers 14 present), and more preferably an angle of about 90° with the surface of the substrate.

As noted previously, variations of the present invention include the use of an intermediate layer 14 (FIGS. 1(B)-(E)), or the formation of the dielectric layer 12 directly on the substrate 10 (FIG. 1(A)). Another variation is that the dielectric layer 14 does not have to be ablated/removed across its entire thickness. That is, in FIG. 1(E), the openings 20 are shown to run across the entire thickness of layer 12 (i.e., from upper surface 12a to and through lower surface 12b), thus exposing the intermediate layer 14 under dielectric layer 12 (or the substrate 10, in instances where no intermediate layer 14 is included). However, if desired, only part of the thickness of layer 12 could be ablated so that the material forming layer 12 remains at the bottom of the opening 20, even to the degree that none of the underlying layer 14 or substrate 10 are exposed.

EXAMPLES

The following examples set forth preferred methods in accordance with the invention. It is to be understood, however, that these examples are provided by way of illustration and nothing therein should be taken as a limitation upon the overall scope of the invention.

Example 1

Formulation of Material 1

In this procedure, 17.30 grams (0.04 mole) of bis(4-(4-aminophenoxy)phenyl) sulfone (TCI America, Portland, Oreg.) was dissolved in 120 mL of dimethylformamide (>99.8% DMF; Sigma Aldrich, Milwaukee, Wis.) and added to a 500-mL reactor vessel (Chemglass, CG-1922-01, Vineland, N.J.). A mechanical stirrer [Fisher Scientific, 501-20511-01-3 with RZR 2051 control, Hampton, N.H.) with 44-cm glass stir shaft (Ace Glass, Vineland, N.J.) was attached and set at 200 rpm. Next, 10.01 grams (0.04 mole) 4,4'-methylenebis(phenyl isocyanate) (Sigma Aldrich, Milwaukee, Wis.) was dissolved in 25 mL of DMF and was added drop wise to the reactor vessel. The reaction proceeded for 24 h, and the polymer was precipitated using deionized (DI) water three times. The final polymer was dried in the vacuum oven at 55° C. for 48 h. The dried polymer was dissolved in 140 mL of gamma-butyrolactone (GBL) (Sigma-Aldrich, St. Louis, Mo.) and filter with a 0.2-μm, ¼" MNPT, vent Meissner Vangard® filter (Meissner Filtration Products, Camarillo, Calif.).

Example 2

Formulation of Material 1A

In this Example, 23.77 grams (0.055 mole) of bis(4-(4-aminophenoxy)phenyl) sulfone was dissolved in 295 mL of GBL and added to a 500-mL reactor vessel. A mechanical stirrer with a 44-cm glass stir shaft was attached and set at 200 rpm. Next, 13.76 grams (0.055 mole) of 4,4'-methylenebis(phenyl isocyanate) was dissolved in 25 mL of GBL and added dropwise to the solution of bis(4-(4-aminophenoxy)phenyl) sulfone. The reaction proceeded for 24 hours and was filtered with a 0.2 μm, ¼" MNPT, vent Meissner Vangard® filter.

Example 3

Preparation of 1,3-bis(4-formylphenoxy)-2-hydroxypropane [4EPIDA]

In this procedure, 320 ml of ethanol (Sigma-Aldrich, St. Louis, Mo.) was charged into a 1000-ml, three-necked, round-bottom flask fitted with a Teflon®-coated stirring bar, nitrogen inlet, and reflux condenser. The flask was immersed in a silicone oil bath seated on a temperature-controlled hot plate/magnetic stirrer. A low nitrogen purge was initiated in the flask, after which 97.70 grams (0.80 mole) of 4-hydroxybenzaldehyde (98%, Sigma-Aldrich, St. Louis, Mo.) was dissolved in the ethanol by stirring. Next, 153.14 grams (0.42 mole) of 25% aqueous TMAH solution (Sigma-Aldrich, St. Louis, Mo.) was added slowly into the solution. After the solution became clear, heat was added to raise the temperature of the reaction to 80° C., and then 37.01 grams (0.40 mole) of epichlorohydrin (≥99%, Sigma-Aldrich, St. Louis, Mo.) dissolved in 80 ml of ethanol was added into the mixture. The contents were then heated to reflux for 12 hours and subsequently cooled to room temperature, after which the product, 4EPIDA, crystallized from the mixture in 80-85% yield (5 batches). After cooling to room temperature, the product was precipitated from the solution, filtered using a Buchner funnel and 500-mL filter flask (Chemglass, Vineland, N.J.) with 90-mm Whatman™ filter paper (11-μm pore size) (GE Healthcare Life Sciences, Little Chalfont, Buckinghamshire, UK) and washed with deionized (DI) water and ethanol (alcohol reagent, anhydrous, denatured, ACS, 94-96%). The final product was dried in a vacuum oven at 55° C. for 48 hours.

Figure 2:
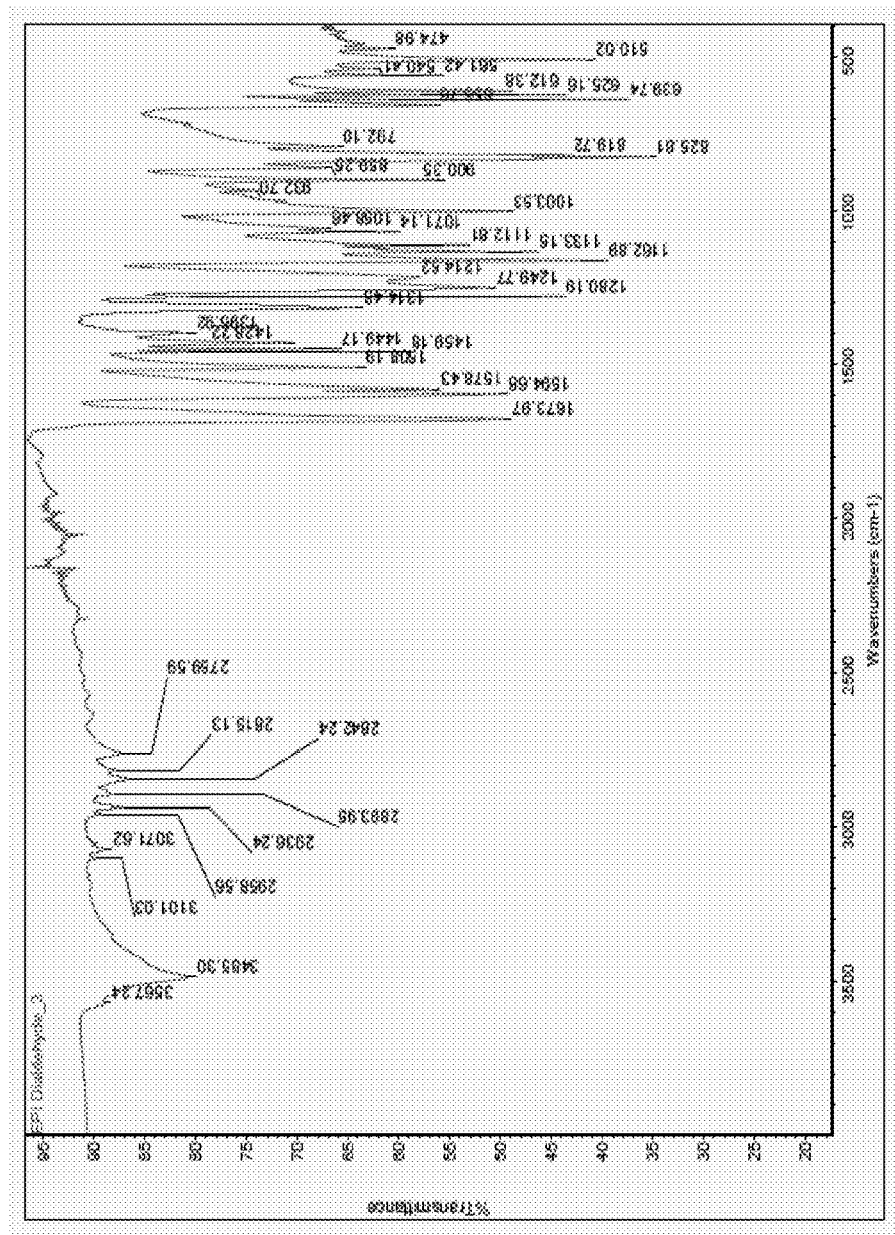
FIG. 2 is an infrared spectrum of the 4EPIDA prepared in Example 3.

The melting points of the batch-wise products as determined by differential scanning calorimetry (DSC) were in the range of 141-144° C. The infrared spectrum for the obtained 4EPIDA product is depicted in FIG. 2. The product's features were consistent with the assignment of a 2-hydroxypropyl-linked, aromatic dialdehyde structure. The structure of 4EPIDA is as follows:

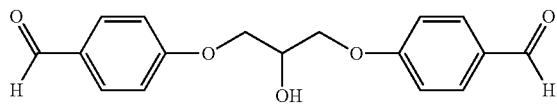 [SMILES: O=Cc1ccc(OCC(O)COc2ccc(C=O)cc2)cc1]

Example 4

Formulation of Material 2

In this Example, 29.42 grams (0.098 mole) of the 4EPIDA synthesized in Example 3 and 19.03 grams (0.098 mole) of isophthalic acid dihydrazide (or "isophthalic dihydrazide"; TCI America, Portland, Oreg.) were added to a 500-mL reactor vessel and dissolved in 140 mL of dimethyl sulfoxide (99+% DMSO; Alfa Aesar, Ward Hill, Mass.). A mechanical stirrer with 44-cm glass stir shaft was attached and set at 200 rpm. Next, 3-4 drops of sulfuric acid (Sigma Aldrich, Milwaukee, Wis.) were added and the reaction was allowed to stir for 24 hours. The solution was filtered using a 0.2-μm, ¼" MNPT, vent Meissner Vangard® filter.

Example 5

Formulation of Material 2A

In this procedure, 65.51 grams of the 4EPIDA synthesized in Example 3 and 42.36 grams of isophthalic acid dihydrazide were dissolved in 392.15 grams of 99+% DMSO. Next, 3-4 drops of trifluoroacetic acid (Alfa Aesar, Ward Hill, Mass.) were added, and the reaction was allowed to stir for 24 hours. The solution was filtered using a 0.2-μm, ¼" MNPT, vent Meissner Vangard® filter (Meissner Filtration Products, Camarillo, Calif.).

Example 6

Formulation of Material 2B

In this Example, 26.46 grams (0.089 mole) of the 4EPIDA synthesized in Example 3 and 17.50 grams (0.089 mole) of isophthalic acid dihydrazide were dissolved in 140 mL of 99+% DMSO. Next, 3-4 drops of sulfuric acid were added, and the reaction was allowed to stir for 24 hours. The solution was filtered using a 0.2-μm, ¼" MNPT, vent Meissner Vangard® filter (Meissner Filtration Products, Camarillo, Calif.).

Example 7

Formulation of Material 2C

In this procedure, 14.20 grams of the 4EPIDA synthesized in Example 3 was added to a 500-mL reactor vessel and dissolved in 99+% DMSO. A mechanical stirrer with 44-cm glass stir shaft was attached and set at 130 rpm. Next, 1.49 grams of 10% trifluoroacetic acid in propylene glycol methyl ether (PGME; Taiwan Maxwave Co., Taipei, Taiwan) were added. Powdered isophthalic acid dihydrazide (8.35 grams; TCI America, Portland, Oreg.) was added and allowed to dissolve. The reaction was allowed to stir overnight and filtered with a 0.2-μm, ¼" MNPT, vent Meissner Vangard® filter.

Example 8

Formulation of Material 2D

In this procedure, 29.48 grams (0.098 mole) of the 4EPIDA synthesized in Example 3 was dissolved in 248.11 grams of 99+% DMSO and added to a 500-mL reactor vessel. A mechanical stirrer with 44-cm glass stir shaft was attached and set at 200 rpm. Next, 3.36 grams of 10% trifluoroacetic acid in PGME was added to the solution. Powdered isophthalic acid dihydrazide (19.06 grams; 0.098 mole) was added, and the reaction was allowed to stir for 24 hours, and filtered using a 0.2-μm, ¼" MNPT, vent Meissner Vangard® filter.

Example 9

Excimer Laser Ablation Results

The materials of Examples 1 and 4 were formed into films and excimer laser ablation was performed by SUSS Micro-Tec. The films were formed by spin-coating the formulations onto 200-mm silicon substrates at 1,500 rpm for 30 seconds, followed by baking at 60° C. for 3 minutes, followed by 100° C. for 10 minutes, and then 250° C. for 30 minutes.

The laser experimental conditions were laser & wavelength: XeCl (308 nm); fluence: 260~1000 mJ/cm$^2$; mask pattern: SUSS resolution test mask; machining method: scan ablation.

Figure 3:
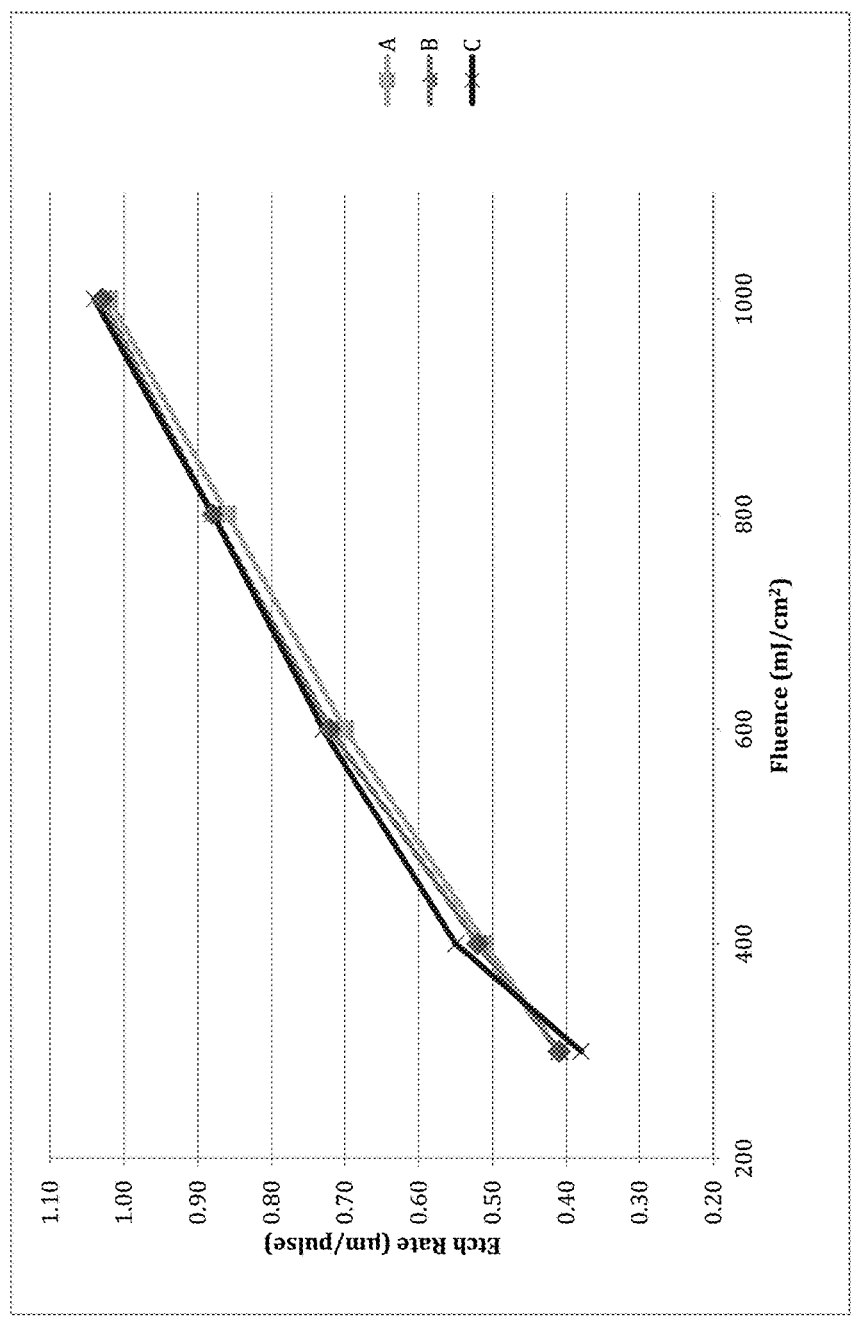
FIG. 3 a graph with an etch rate comparison of the Example 1 formulation (circles) and Example 4 formulation (squares)

Tables 1 and 2 show the etch rates for Material 1 and Material 2, respectively, and FIG. 3 is a graph comparing those etch rates.

TABLE 1

Parameters for Material from Example 1

| Fluence (mJ/cm$^2$) | Via size (μm) | Thickness (μm) | Pulse | Etch rate (μm/pulse) |
|---|---|---|---|---|
| 1000 | 20 | 17.6 | 17 | 1.04 |
| 800 | 20 | 17.6 | 20 | 0.88 |
| 600 | 20 | 17.6 | 24 | 0.73 |
| 400 | 20 | 17.6 | 32 | 0.55 |
| 300 | 20 | 17.6 | 46 | 0.38 |

TABLE 2

Parameters for Material from Example 4

| Fluence (mJ/cm$^2$) | Via size (μm) | Thickness (μm) | Pulse | Etch rate (μm/pulse) |
|---|---|---|---|---|
| 1000 | 20 | 11.2 | 11 | 1.02 |
| 800 | 20 | 11.2 | 13 | 0.86 |
| 600 | 20 | 11.2 | 16 | 0.70 |
| 400 | 20 | 11.2 | 22 | 0.51 |
| 300 | 20 | 11.2 | 27 | 0.41 |

Figure 4:
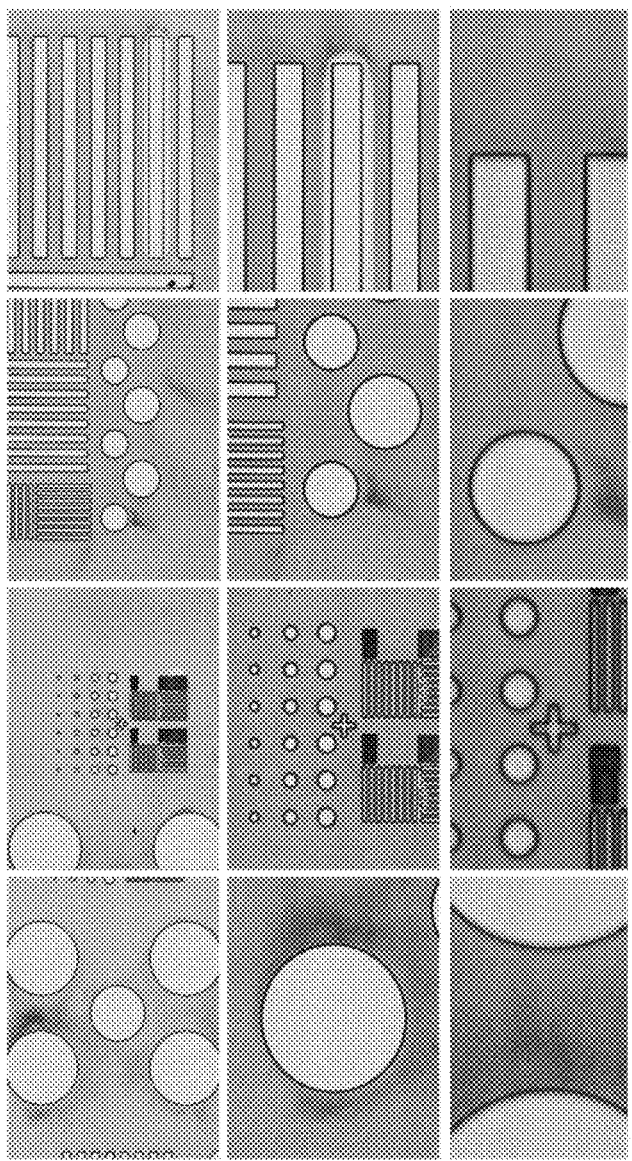
FIG. 4 shows optical microscopy photos of the laser ablative patterning of the Example 1 formulation prior to cleaning.
Figure 5:
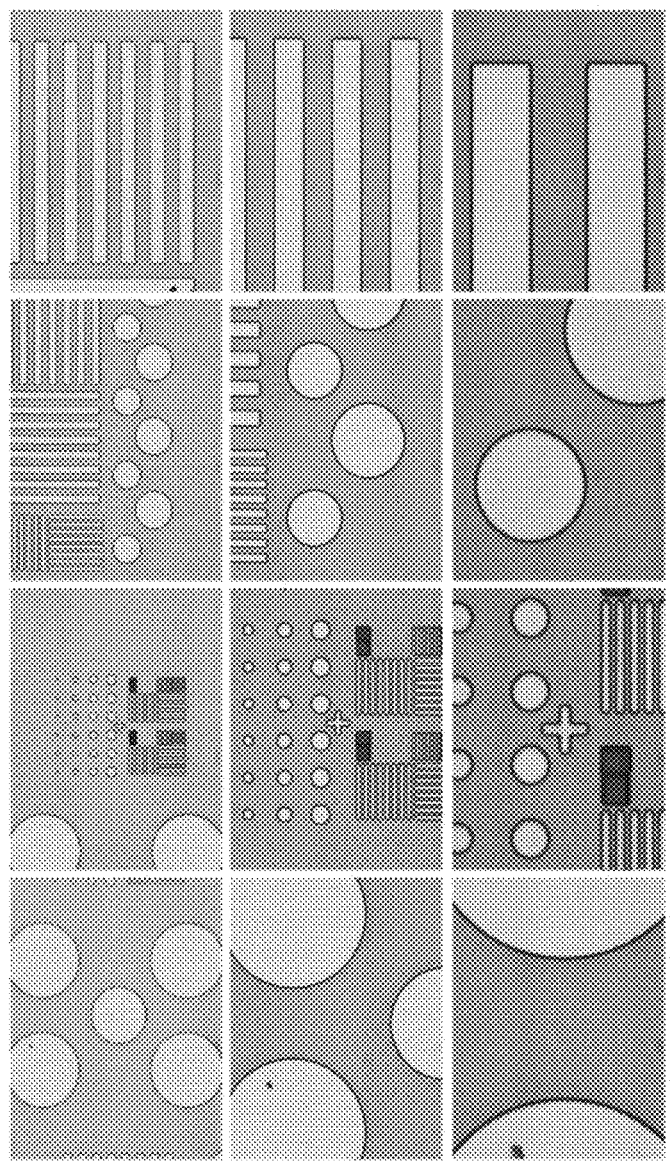
FIG. 5 provides optical microscopy photos of the laser ablative patterning of the Example 4 formulation prior to cleaning.

FIGS. 4-5 are images from optical microscopy of the amount of residual debris left on silicon wafers after laser ablation. FIG. 4 shows particle-like debris adjacent to the ablated features, Si wafer coated with Material 1; F=1000 mJ/cm$^2$, N=24, where F is the fluence and N is the number of pulses. FIG. 5 shows the ablated features with no debris, Si wafer coated with Material 2; F=1000 mJ/cm$^2$, N=15.

Figure 6:
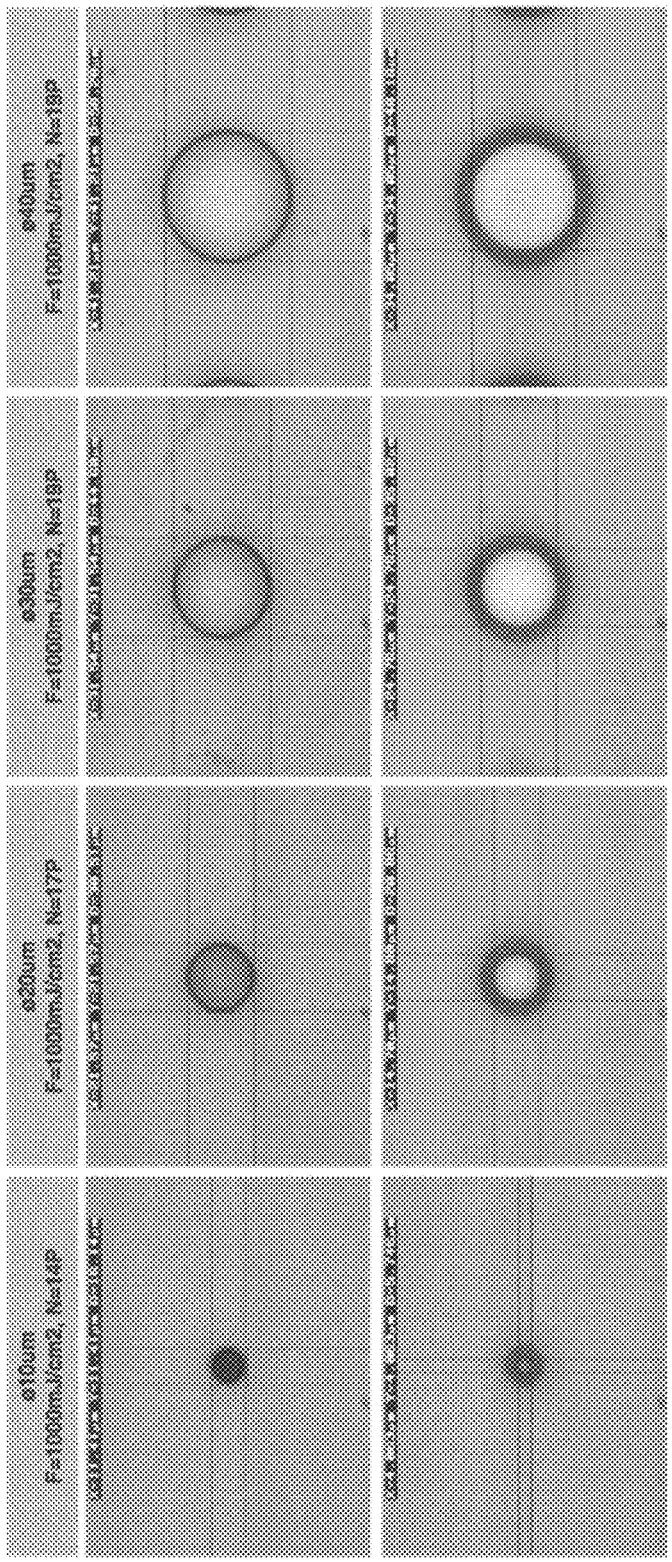
FIG. 6 shows optical microscopy photos of vias created by laser ablative patterning of the Example 1 formulation.
Figure 7:
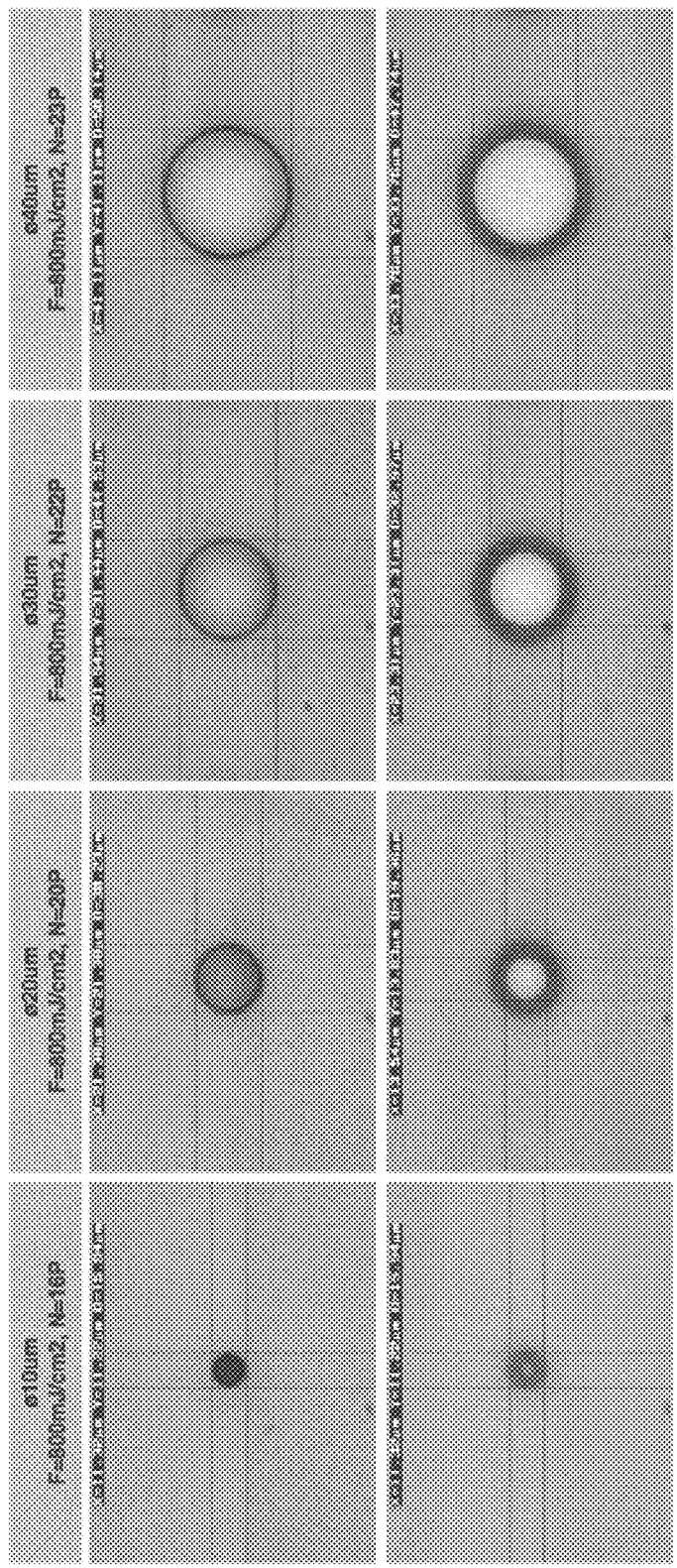
FIG. 7 provides optical microscopy photos of vias created by laser ablative patterning of the Example 1 formulation.
Figure 8:
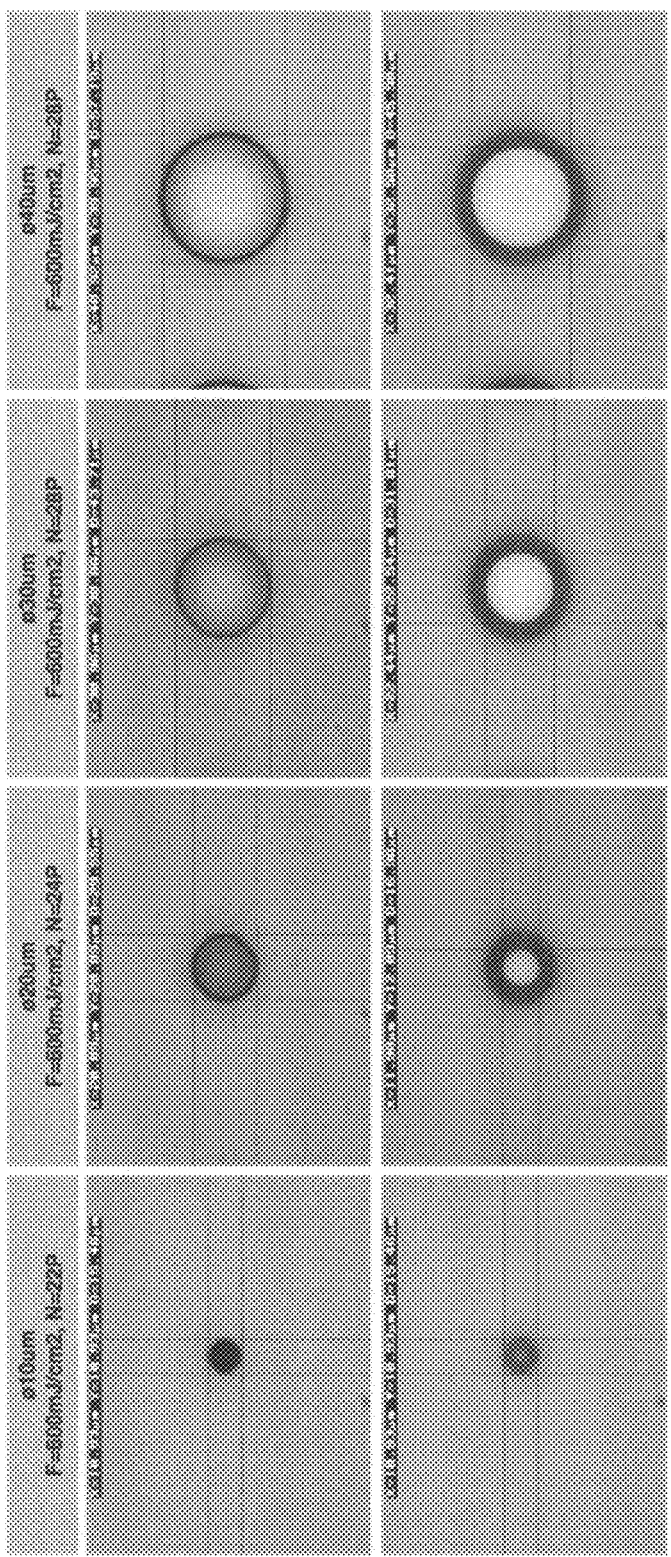
FIG. 8 shows optical microscopy photos of vias created by laser ablative patterning of the Example 1 formulation.
Figure 9:
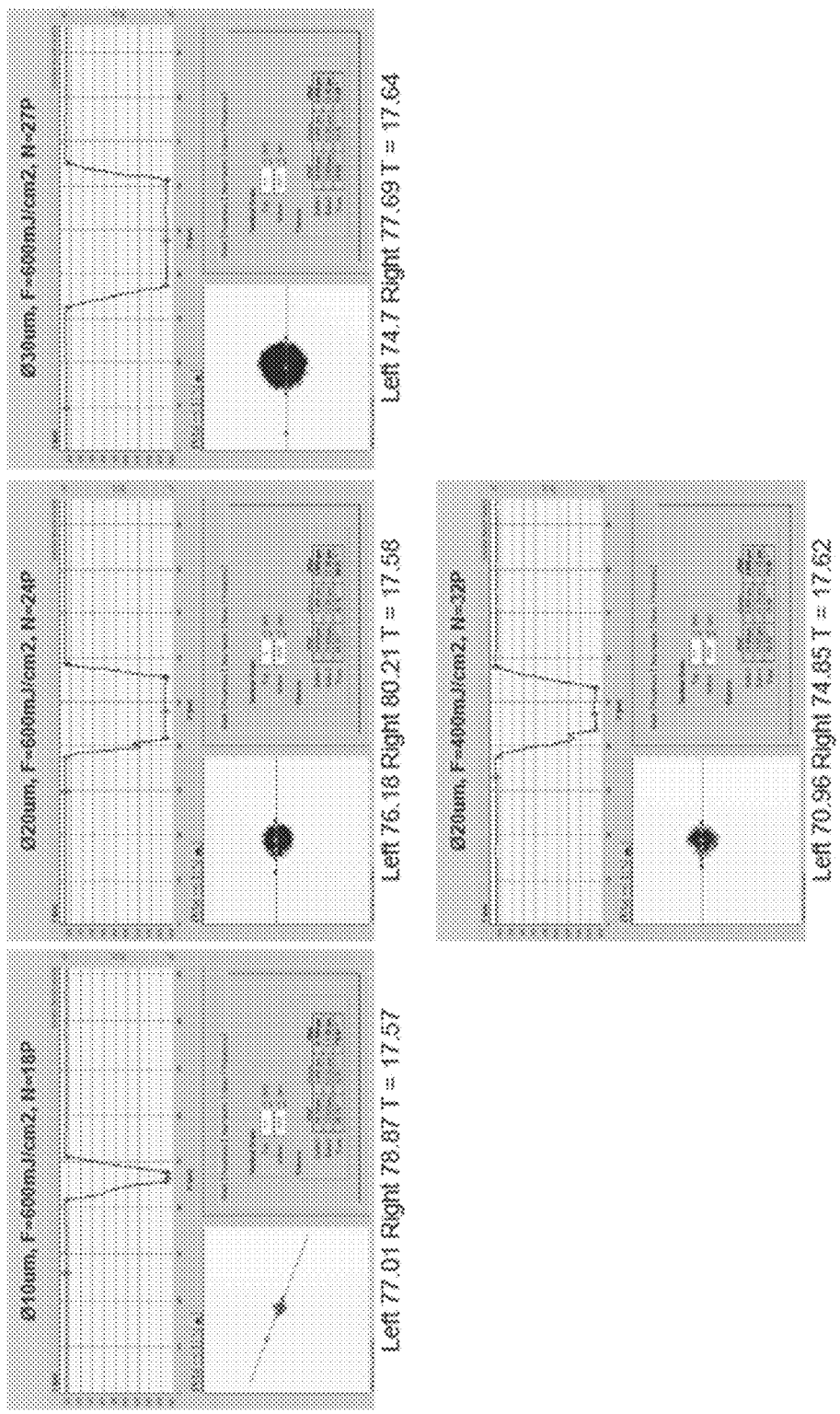
FIG. 9 depicts the profiles of vias created with the Example 1 formulation.
Figure 10:
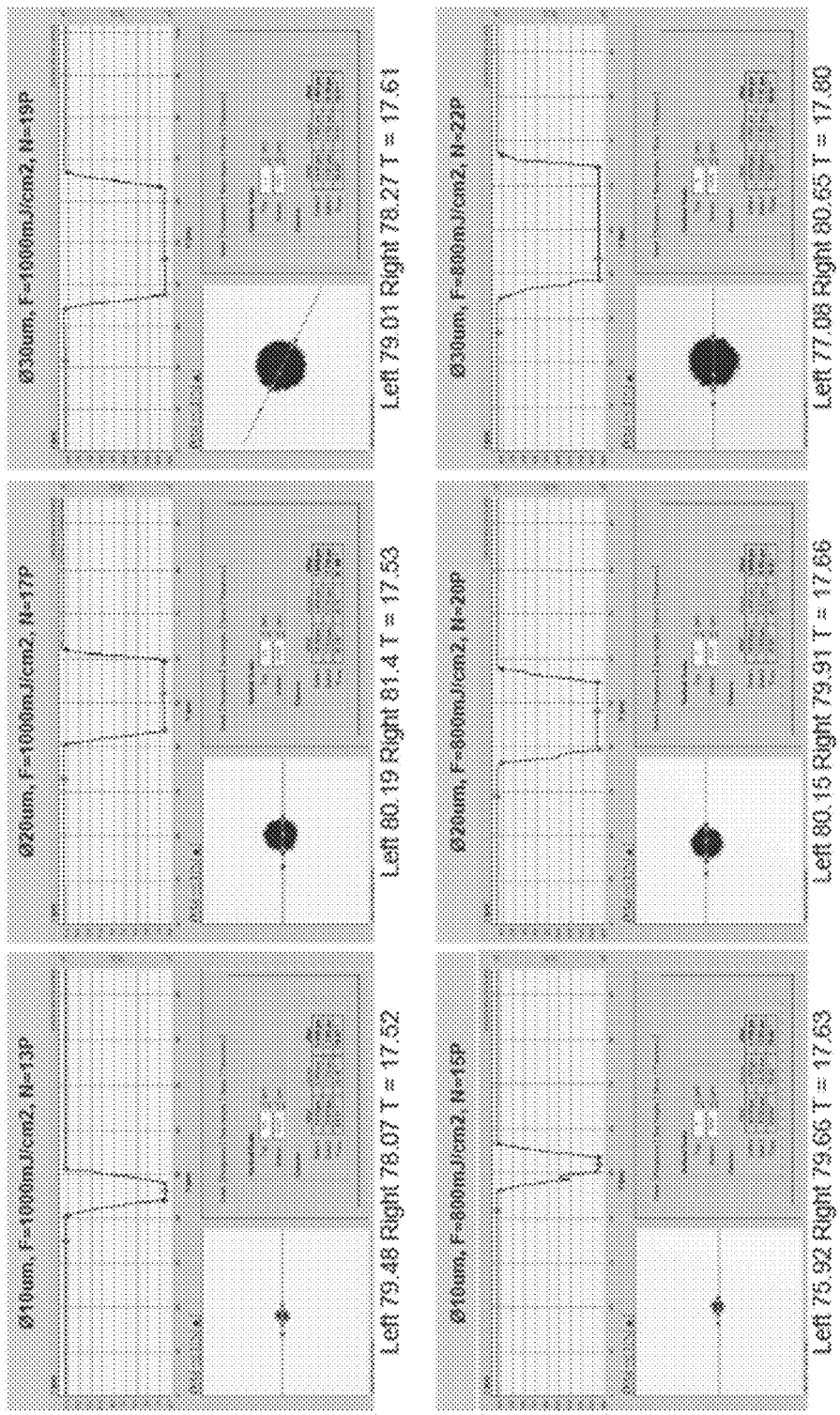
FIG. 10 depicts the profiles of vias created with the Example 1 formulation.
Figure 11:
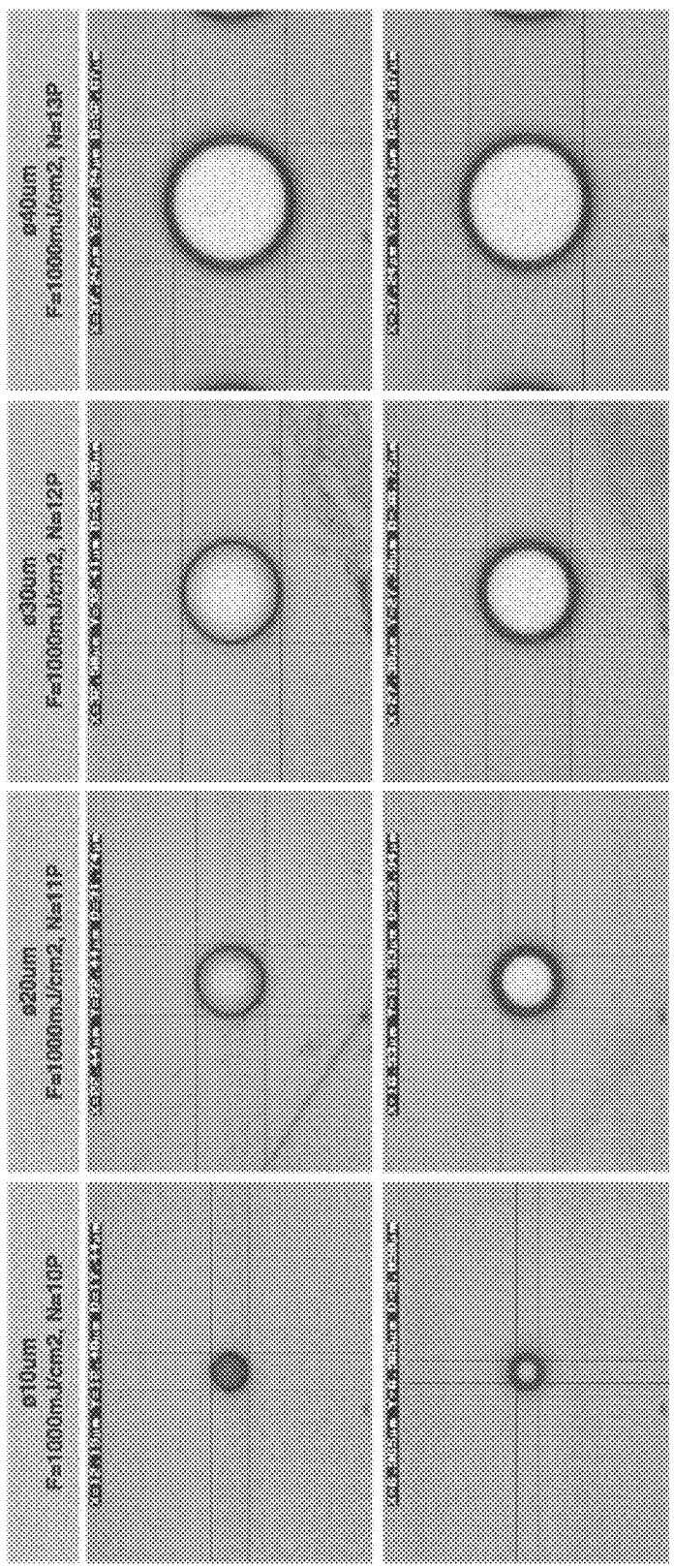
FIG. 11 shows optical microscopy photos of vias created by laser ablative patterning of the Example 4 formulation.
Figure 12:
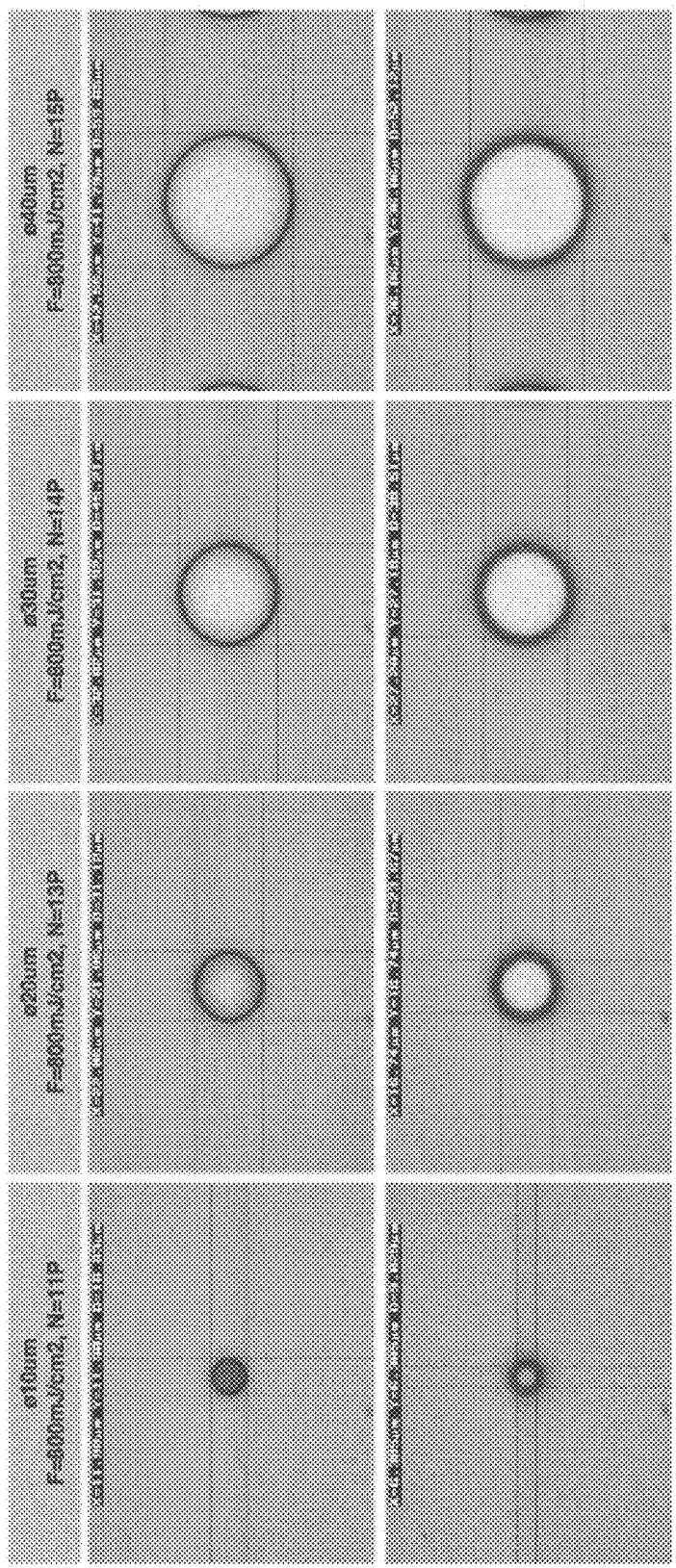
FIG. 12 provides optical microscopy photos of vias created by laser ablative patterning of the Example 4 formulation.
Figure 13:
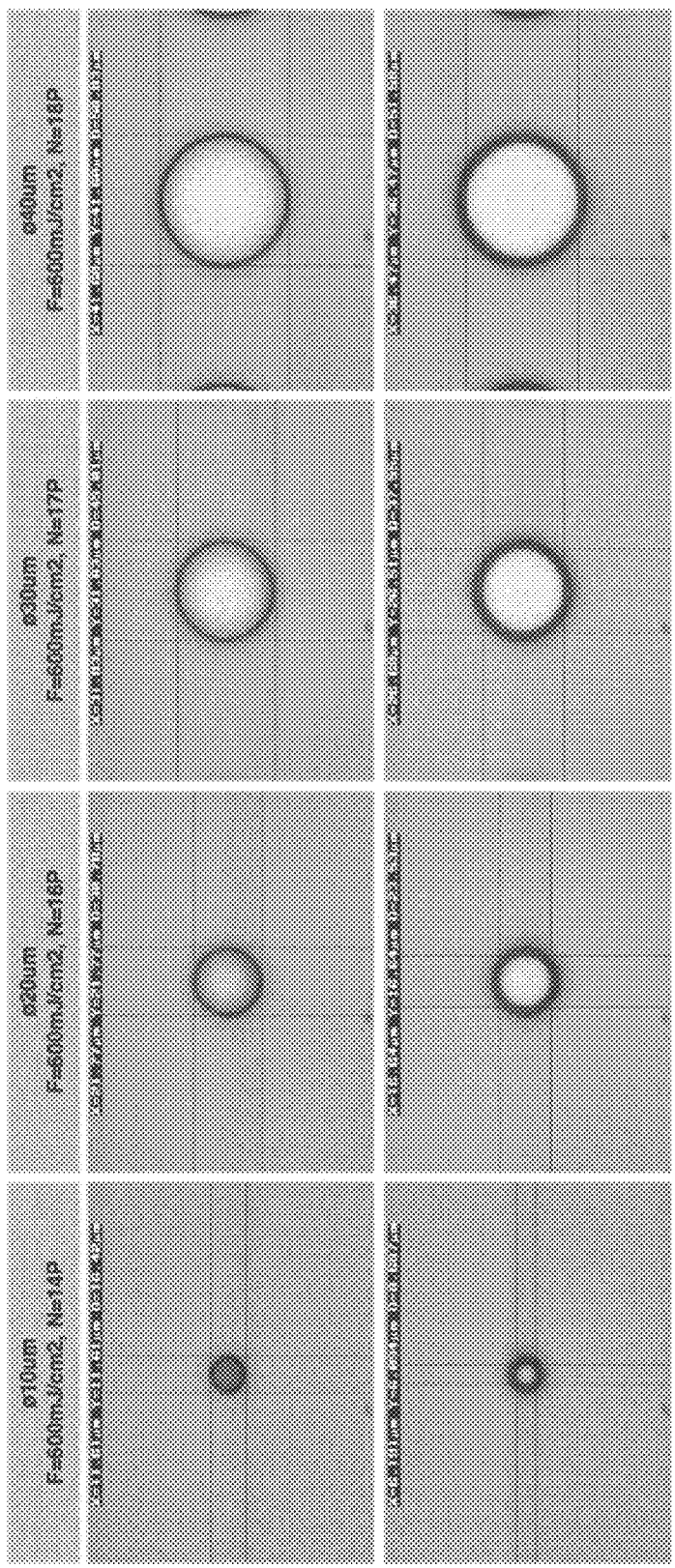
FIG. 13 shows optical microscopy photos of vias created by laser ablative patterning of the Example 4 formulation.
Figure 14:
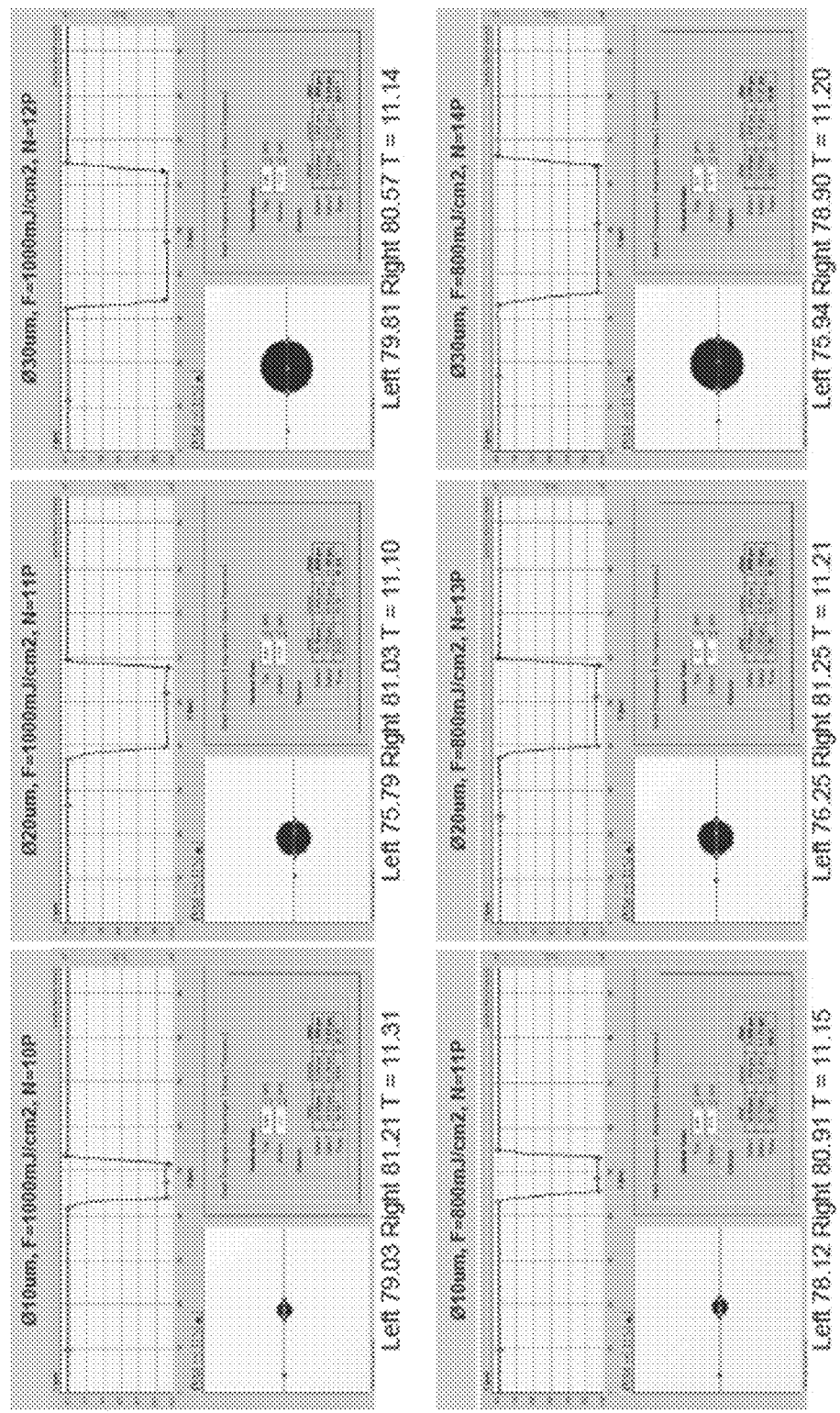
FIG. 14 depicts the profiles of vias created with the Example 4 formulation.
Figure 15:
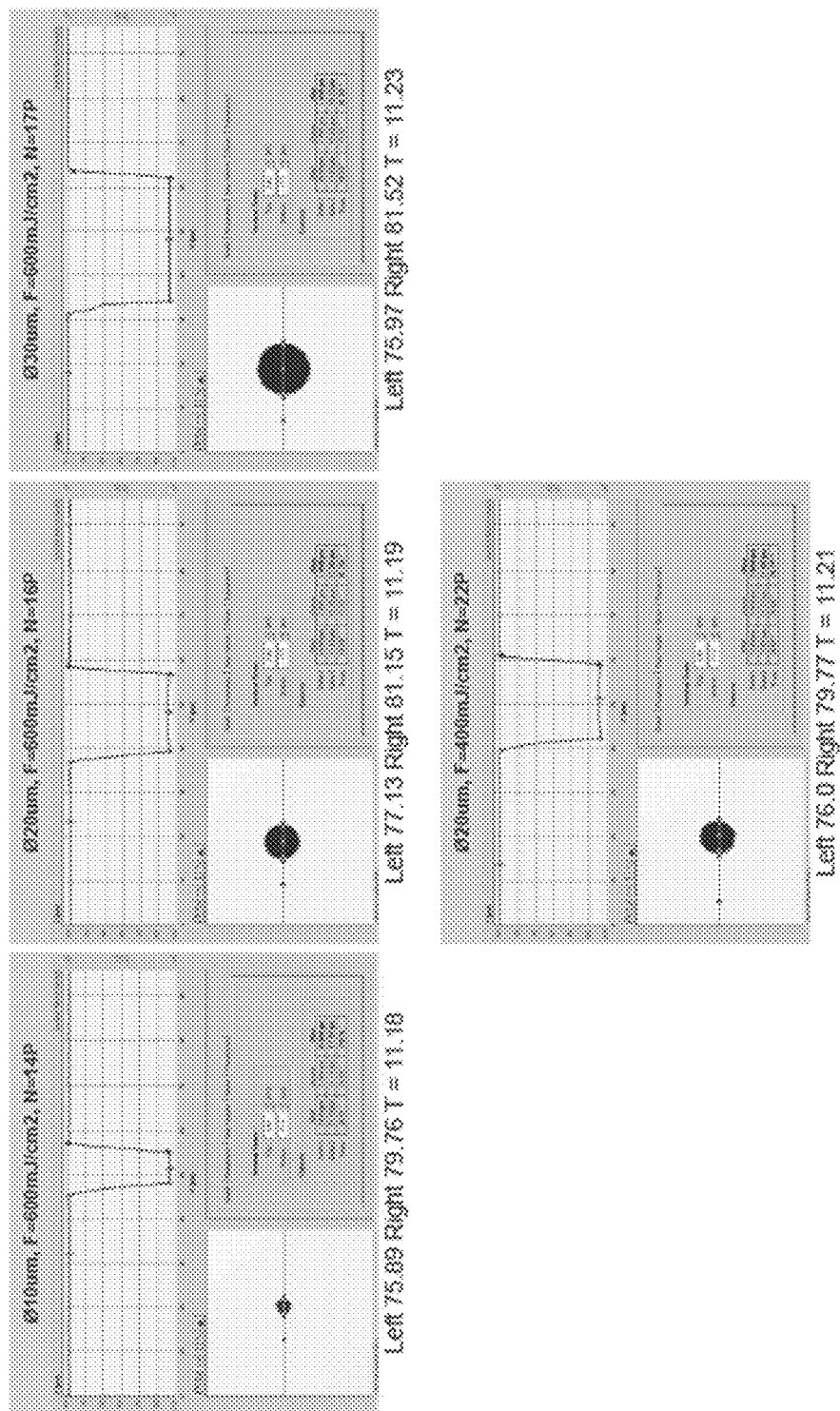
FIG. 15 depicts the profiles of vias created with the Example 4 formulation.

FIGS. 6-8 show the ablation quality for vias created with patterning of Material 1. FIGS. 9-10 show the via profile of Material 1. FIGS. 11-13 show the ablation quality for vias created by patterning Material 2. FIGS. 14-15 are the via profiles, which include sidewall angles for Material 2.

Comparative Example 10

Reaction of Isophthalic Acid Dihydrazide and Terephthalic Acid

In this comparative procedure, 4.272 grams (22 mmoles) of isophthalic acid dihydrazide (>95% [HPLC]) and 2.956 grams (22 mmoles) of terephthalic acid (Sigma-Aldrich, St. Louis, Mo.) were weighed into a glass vial fitted with a screw cap and a stirring bar for agitation. Next, 20 grams of DMSO were added to the container to adjust the final polymer solids level. The contents were stirred at room temperature to disperse the reactants and 1-2 drops of acetic acid were added to catalyze the polymerization reaction. Shortly after the addition of the acid catalyst, a mild exotherm was observed, and the solution clarified quickly and became noticeably more viscous. The solution formed an insoluble paste within minutes.

Comparative Example 11

Reaction of Terephthalaldehyde, Adipic Acid Dihydrazide, and Isophthalic Acid Dihydrazide In this comparative Example, 1.916 grams (11 mmoles) of adipic acid dihydrazide, 2.136 grams (11 mmoles) of isophthalic acid dihydrazide, and 2.956 grams (22 mmoles) of terephthalaldehyde were weighed into a glass vial fitted with a screw cap and a stirring bar for agitation. Next, 20 grams of DMSO was added to the container to adjust the final polymer solids level. The contents were stirred at room temperature to disperse the reactants, and 1-2 drops of acetic acid were added to catalyze the polymerization reaction. Shortly after the addition of the acid catalyst, a mild exotherm was observed, and the solution clarified quickly and became noticeably more viscous. The solution formed an insoluble paste over the course of 1-2 days.

Example 12

Copolymer of Adipic Acid Dihydrazide and 4EPIDA

In this Example, 7.16 grams (41 mmoles) of adipic acid dihydrazide and 12.31 grams (41 mmoles) of the 4EPIDA prepared in Example 3 were combined in 75.00 g of DMSO in a glass vial to form an 18 wt. % polymer solution (corrected for water produced in the polymerization reaction). After a few drops of concentrated acetic acid were added to catalyze the reaction, the contents were stirred for 12 hours at room temperature to form a viscous, transparent polyacylhydrazone solution.

The spontaneous decomposition temperature ($T_d$) of the product by ramp thermogravimetric analysis (TGA @ 10° C./min under nitrogen) was 335° C. The glass transition temperature ($T_g$) of the polymer as taken from the tan delta maximum in the melt rheology curve was 160° C. The molecular weight characteristics of the product as determined by gel permeation chromatography (GPC) were as follows: weight average molecular weight ($M_w$)=28,500; number average molecular weight ($M_n$)=15,700; polydispersity (PD)=1.82.

A second batch was prepared similarly using purified 4EPIDA. The 4EPIDA was purified by recrystallizing the product formed in Example 3. The recrystallization procedure involved suspending about 250 g of the product from Example 3 in about 750 ml of 4:1 v/v mixture of ethanol and water, heating to dissolve the product, and then cooling to room temperature to cause the purified product to crystallize from the solution in about 70% yield. The resulting polymer had a $M_w$ of 44,700, $M_n$ of 19,800, and PD of 2.2. Furthermore, the melting point had narrowed to 141-142° C. in the recrystallized product. However, the repeating unit of the structure did not change during this process. The copolymer had the following structure:

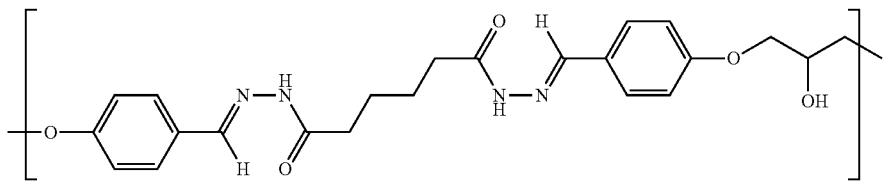

Example 13

Copolymer of Adipic Acid Dihydrazide and 4EPIDA

In this Example, 7.16 grams (41 mmoles) of adipic acid dihydrazide and 12.33 grams (41 mmoles) of the 4EPIDA prepared in Example 3 were combined in 75.00 grams of DMSO in a glass vial to form an 18 wt. % polymer solution. After a few drops of concentrated sulfuric acid were added to catalyze the polymerization reaction, the contents were stirred for 12 hours at room temperature to form a viscous, transparent polyacylhydrazone solution. The molecular weight characteristics of the product as determined by GPC were as follows: $M_w$=30700; $M_n$=15,200; PD=2.02.

Example 14

Copolymer of Adipic Acid Dihydrazide and 4EPIDA

Figure 16:
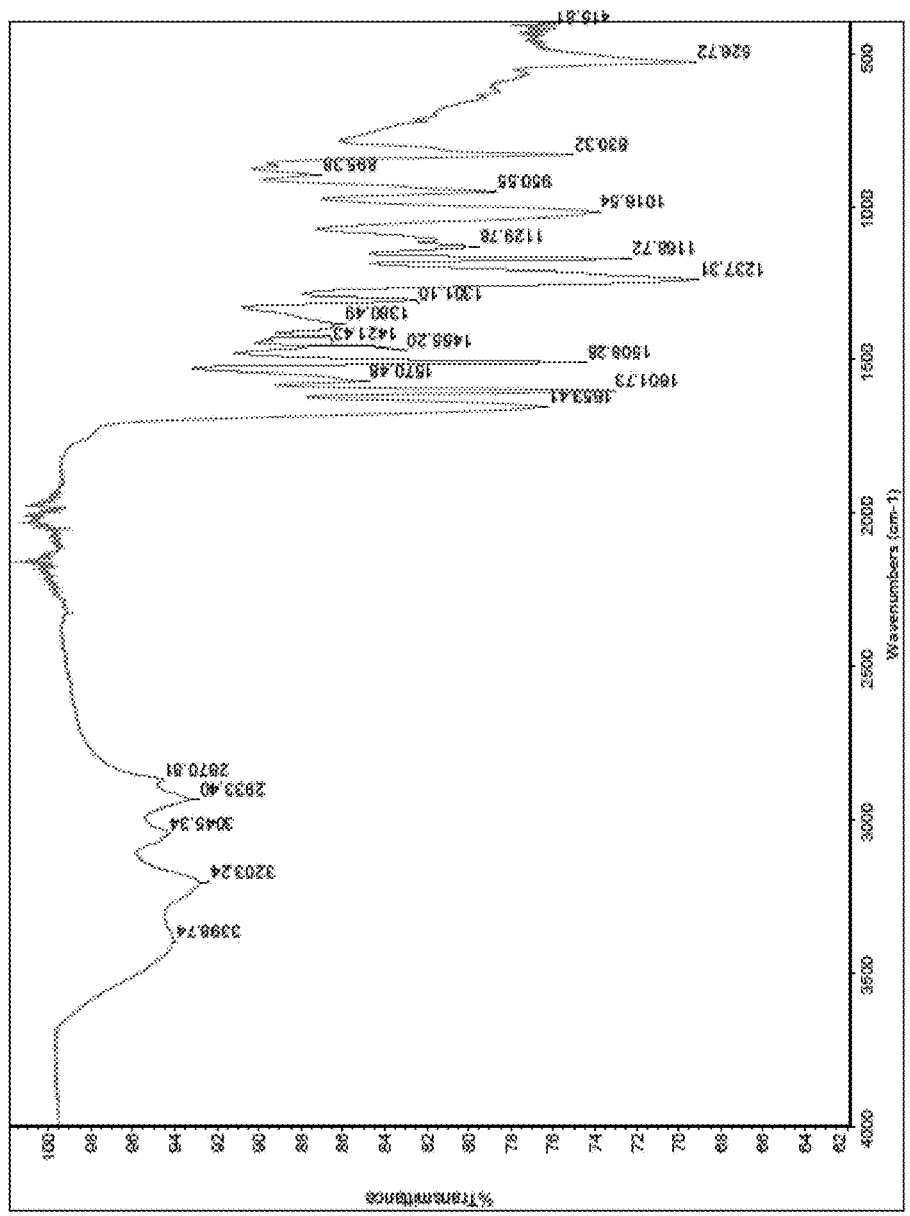
FIG. 16 is the FTIR spectrum of the adipic acid dihydrazide and 4EPIDA copolymer prepared in Example 14.

In this Example, 5.959 grams (34.2 mmoles) of adipic acid dihydrazide and 10.274 grams (34.2 mmoles) of the 4EPIDA prepared in Example 3 were combined in 33.83 grams of DMSO in a plastic bottle to form a 30 wt. % polymer solution. After a few drops of concentrated sulfuric acid were added to catalyze the polymerization reaction, the contents were stirred for 12 hours at room temperature to form a viscous, transparent polyacylhydrazone solution. The features of the FTIR spectrum of the precipitated polymer (shown in FIG. 16) were consistent with the expected structure.

A small amount of the polymer solution was precipitated in methanol and then subjected to soxhlet extraction overnight with methanol to remove the last traces of the solvent and impurities. The resulting solid, leathery polymer mass was then dried in a vacuum oven at 60° C. The $T_d$ of the extracted product by ramp TGA was 331° C.

The molecular weight characteristics of the product as determined by GPC were as follows: $M_w$=85,300; $M_n$=39,900; and PD=2.14. As a measure of the storage stability of the polyacylhydrazone product, a portion of the solution was stored in a sealed container at room temperature for about 4 months during which it remained transparent and pourable. The product molecular weight characteristics were then re-characterized by GPC as follows: $M_w$=97,300; $M_n$=31,200; and PD=3.12, which indicated that no chain degradation was occurring over time. A second batch of the polymer was prepared under the same conditions as the first. The polymer molecular weight characteristics of the second batch were very comparable to those of the first: $M_w$=90,300; $M_n$=35,000; and PD=2.58.

A thick film of the polyacylhydrazone was spin-cast from the solution onto a silicon wafer treated with a release agent (BREWERBOND® 510, Brewer Science, Inc., Rolla, Mo.) so that it could be easily peeled off after multi-stage baking to 200° C. to remove the solvent. Dynamic mechanical analysis of the film produced a value of 1150 MPa for the Young's Modulus of the polymer. Elongation at break was 49%.

Example 15

Copolymer of Isophthalic Acid Dihydrazide and 4EPIDA

In this procedure, 4.236 grams (21.8 mmoles) of isophthalic acid dihydrazide and 6.555 grams (21.8 mmoles) of the 4EPIDA prepared in Example 3 were combined in 39.26 grams of DMSO in a plastic bottle to form a 20 wt. % polymer solution. After a few drops of concentrated sulfuric acid were added to catalyze the polymerization reaction, the contents were stirred for 12 hours at room temperature to form a viscous, transparent polyacylhydrazone solution.

Figure 17:
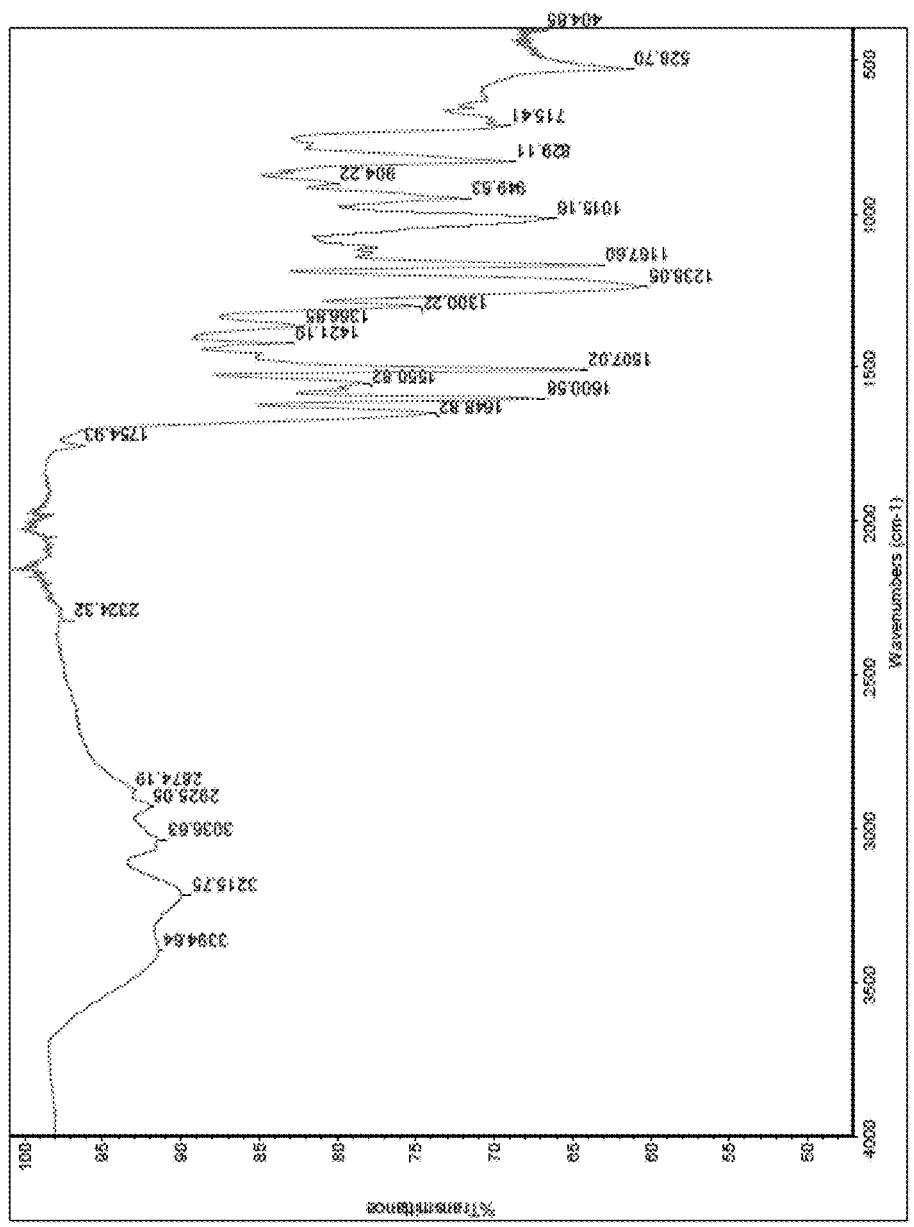
FIG. 17 is the FTIR spectrum of the isophthalic acid dihydrazide and 4EPIDA copolymer prepared in Example 15.

The $T_d$ of the product by ramp TGA at 10° C./min under nitrogen was 351° C. The polymer $T_g$ taken from the tan delta maximum in the melt rheology curve was 228° C. The molecular weight characteristics of the product as determined by GPC were as follows: $M_w$=78,500; $M_n$=40,500; and PD=1.94. The FTIR spectrum of the polymer is depicted in FIG. 17 and was consistent with the expected polyacylhydrazone structure. The copolymer had the following structure:

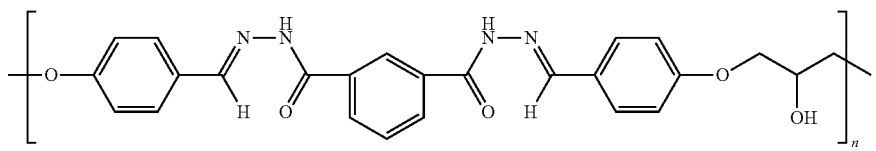

Example 16

Terpolymer of Adipic Acid Dihydrazide, Isophthalic Acid Dihydrazide, and 4EPIDA In this procedure, 1.942 grams (11.1 mmoles) of adipic acid dihydrazide, 2.166 grams (11.2 mmoles) of isophthalic acid dihydrazide, and 6.695 grams (22.3 mmoles) of 4EPIDA were combined in 39.27 grams of DMSO in a plastic bottle to form a 20 wt. % polymer solution. After a few drops of concentrated sulfuric acid were added to catalyze the polymerization reaction, the contents were stirred for 12 hours at room temperature to form a viscous, transparent polyacylhydrazone solution. The molecular weight characteristics of the product as determined by GPC were as follows: $M_w$=74,500; $M_n$=33,800; and PD=2.21.

Example 17

Terpolymer of Isophthalic Acid Dihydrazide, 4EPIDA, and Terephthalaldehyde

In this Example, 4.657 grams (24.0 mmoles) of isophthalic acid dihydrazide, 5.403 grams (18.0 mmoles) of the 4EPIDA prepared in Example 3, and 0.804 grams (6.0 mmoles) of terephthalaldehyde were combined in 39.14 grams of DMSO in a plastic bottle to form a 20 wt. % polymer solution. After a few drops of concentrated sulfuric acid were added to catalyze the polymerization reaction, the contents were stirred for 12 hours at room temperature to form a viscous, transparent polyacylhydrazone solution. The molecular weight characteristics of the product as determined by GPC were as follows: $M_w$=70,800; $M_n$=35,400; and PD=2.00. A portion of the solution was stored for >6 months at room temperature in a closed vial and then reexamined. The solution was still fluid and pourable but had developed a hazy appearance.

Example 18

Copolymer of Carbohydrazide and 4EPIDA

In this Example, 1.21 grams (13.4 mmoles) of carbohydrazide (>98%, Sigma-Aldrich, St. Louis, Mo.) and 4.06 grams (13.5 mmoles) of the 4EPIDA prepared in Example 3 were combined in 20.19 grams of DMSO in a glass vial to form a 19 wt. % polymer solution. After a few drops of concentrated sulfuric acid were added to catalyze the polymerization reaction, the contents were stirred for 12 hours at room temperature to form a viscous, transparent polyacylhydrazone solution. The molecular weight characteristics of the product as determined by GPC were as follows: $M_w$=33,400; $M_n$=16,800; and PD=1.98. A portion of solution was stored for >6 months at room temperature in a closed vial and then reexamined. The solution was still fluid and pourable but had developed a hazy appearance.

Example 19

Preparation of 1,3-Bis(3-formylphenoxy)-2-hydroxypropane [3EPIDA]

Figure 18:
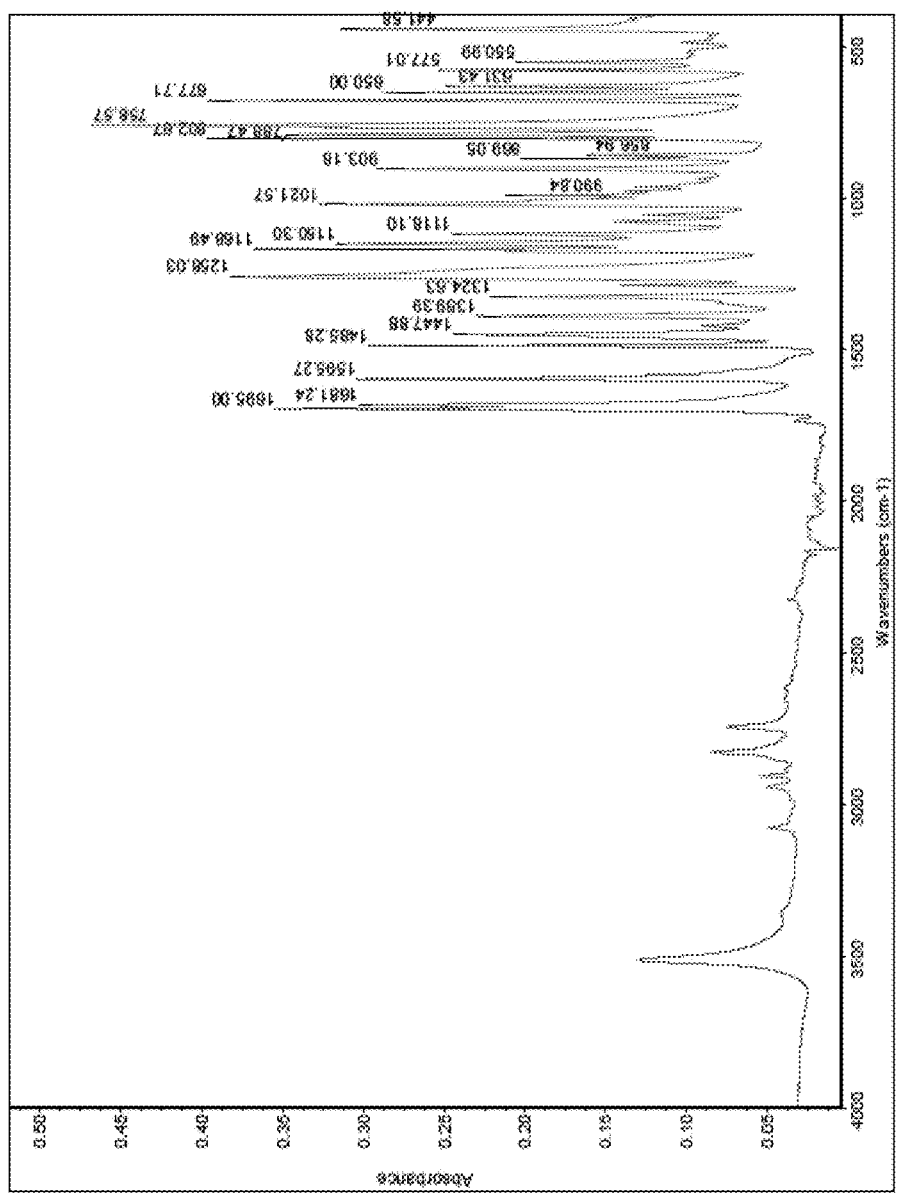
FIG. 18 is an infrared spectrum of the 3EPIDA prepared in Example 19.

In this procedure, 3EPIDA was prepared analogously to 4EPIDA (see Example 3) using 3-hydroxybenzaldehyde (≥99%; Sigma-Aldrich) in place of 4-hydroxybenzaldehyde. The yield of crystalline product from the reaction was 78.2%. The melting point of the product by DSC was 89° C. The infrared spectrum for the obtained 3EPIDA product is depicted in FIG. 18. Its features are consistent with the assignment of a 2-hydroxypropyl-linked aromatic dialdehyde structure. The structure of 3EPIDA is as follows:

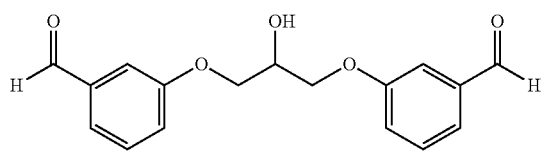 [SMILES: O=Cc1cccc(OCC(O)COc2cccc(C=O)c2)c1]

Example 20

Copolymer of Adipic Acid Dihydrazide and 3EPIDA

In this procedure, 5.959 grams (34.2 mmoles) of adipic acid dihydrazide and 10.270 grams (34.2 mmoles) of 3EPIDA prepared in Example 18 were combined in 33.84 grams of DMSO in a plastic bottle to form a 30 wt. % polymer solution. After a few drops of concentrated sulfuric acid were added to catalyze the polymerization reaction, the contents were stirred for 24 hours at room temperature to form a viscous, transparent polyacylhydrazone solution.

The $T_d$ of the product by ramp TGA at 10° C./min under nitrogen was 302° C. The polymer $T_g$ taken from the tan delta maximum in the melt rheology curve was 142° C. The molecular weight characteristics of the product as determined by GPC immediately following the preparation were as follows: $M_w$=73,000; $M_n$=22,200; and PD=3.30. After three days the molecular weight had equilibrated to the following values: $M_w$=51,500; $M_n$=18,900; and PD=2.72.

Example 21

Copolymer of Isophthalic Acid Dihydrazide and 3EPIDA

In this procedure, 6.64 grams (34.2 mmoles) of isophthalic acid dihydrazide and 10.27 grams (34.2 mmoles) of 3EPIDA prepared in Example 18 were combined in 33.82 grams of DMSO in a plastic bottle to form a 31 wt. % polymer solution. After a few drops of concentrated sulfuric acid were added to catalyze the polymerization reaction, the contents were stirred for 24 hours at room temperature to form a viscous, transparent polyacylhydrazone solution. The molecular weight characteristics of the product as determined by GPC were as follows: $M_w$=83,500; $M_n$=31,500; and PD=2.65.

Example 22

Copolymer of Terephthalic Acid Dihydrazide and 3EPIDA

In this Example, 1.95 grams (10.0 mmoles) of terephthalic acid dihydrazide (TCI America, Portland, Oreg.) and 3.01 grams (10.0 mmoles) of 3EPIDA prepared in Example 18 were combined in 19.11 grams of DMSO in a plastic bottle to form a 19 wt. % polymer solution. After a few drops of concentrated sulfuric acid were added to catalyze the polymerization reaction, the contents were stirred for 24 hours at room temperature to form a viscous, transparent polyacylhydrazone solution. The molecular weight characteristics of the product as determined by GPC were as follows: $M_w$=64,600; $M_n$=26,900; and PD=2.40.

A corresponding all-para-linked polyacylhydrazone was prepared from terephthalic acid dihydrazide and 4EPIDA. It was initially soluble in DMSO but began precipitating as a white, waxy solid within 24 hours after preparation.

Example 23

Preparation of 1,3-Bis(4-formyl-2-methoxyphenoxy)-2-hydroxypropane [VANDA]

In this Example, VANDA was prepared analogously to 4EPIDA prepared in Example 3, but using vanillin in place of 4-hydroxybenzaldehyde. Ethanol (240 g) was charged into a 1000-ml, three-necked, round bottom flask fitted with a Teflon®-coated stirring bar, nitrogen inlet, and reflux condenser. The flask was immersed in a silicone oil bath seated on a temperature-controlled hot plate/magnetic stirrer. A low nitrogen purge was initiated in the flask, after which 91.31 g (0.60 moles) of vanillin (>99%; Sigma-Aldrich) was dissolved in the ethanol by stirring. Next, 114.91 g (0.315 moles) of 25% aqueous TMAH was added slowly into the solution. Once the solution clarified, 27.76 g (0.30 moles) of epichlorohydrin 99%; Sigma-Aldrich) dissolved in 62.2 g of ethanol was added into the mixture. The contents were then heated to 80° C. for 20 hours and subsequently cooled to room temperature after which the product, VANDA, crystallized from the mixture. It was collected by filtration, washed with deionized water and cold ethanol, and then dried in a vacuum oven for 48 hours at 55° C. The yield of powdery, white product from the reaction was ~94%. The melting point of the product by DSC was 139° C. The structure of VANDA is as follows:

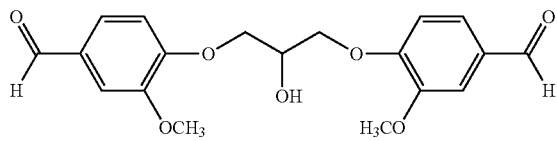

Example 24

Copolymer of Adipic Acid Dihydrazide and VANDA

In this procedure, 1.752 grams (10.1 mmoles) of adipic acid dihydrazide and 3.614 grams (10.0 mmoles) of VANDA prepared in Example 23 were combined in 19.6 g of DMSO in a plastic bottle to form a 20 wt. % polymer solution. After two small drops of concentrated sulfuric acid were added to catalyze the polymerization reaction, the contents quickly clarified, forming a transparent polyacylhydrazone solution that was stirred for 12 hours at room temperature to complete the polymerization.

Example 25

Copolymer of Isophthalic Acid Dihydrazide and VANDA

In this Example, 1.878 grams (9.7 mmoles) of isophthalic acid dihydrazide and 3.475 grams (9.6 mmoles) of VANDA prepared in Example 23 were combined in 19.6 grams of DMSO in a plastic bottle to form a 20 wt. % polymer solution. After two small drops of concentrated sulfuric acid were added to catalyze the polymerization reaction, the contents quickly clarified but then after about 30 minutes formed a waxy gel. Additional DMSO (25.1 grams) was stirred into the reaction mixture to reduce the polymer concentration to 10 wt. %. However, the polymer did not dissolve even after overnight agitation.

The insolubility of the polymer prepared with IDH-VANDA copolymer stands in contrast to the good solubility of the IDH-4EPIDA copolymer described in Example 7. As shown in previous structures, the structure of VANDA and 4EPIDA differ only in that VANDA has a methoxy (—OCH$_3$) substituent adjacent to the ether linking group on each of its rings.

Example 26

Copolymer of Oxalyldihydrazide and 3EPIDA

In this procedure, 1.543 grams (13.1 mmoles) of oxalyldihydrazide (98%, Alfa Aesar, Ward Hill, Mass.) and 3.928 grams (13.1 mmoles) of 3EPIDA prepared in Example 18 were combined in 19.5 grams of DMSO in a plastic bottle to form a 20 wt. % polymer solution. After two small drops of concentrated sulfuric acid were added to catalyze the polymerization reaction, the contents were stirred for 12 hours at room temperature to form an exceedingly viscous, transparent polyacylhydrazone solution. The solution was stored for about one week at room temperature. After that time, it was still fluid but had begun to develop turbidity, indicating the possible onset of slow precipitation.

On the other hand, when the preparation of the corresponding all-para-linked polyacylhydrazone from oxalyldihydrazide and 4EPIDA was attempted at 20 wt. % polymer solids, the monomers reacted quickly after the addition of sulfuric acid catalyst to form a light yellow polymer precipitate almost immediately. Diluting the reaction mixture to 10 wt. % with additional DMSO, followed by overnight agitation, did not cause the polymer precipitate to dissolve. The results of this Example and Example 13 demonstrated the superior solubility-enhancing characteristics of 3EPIDA versus the para-linked 4EPIDA when using dihydrazides such as oxalyldihydrazide and terephthalic acid dihydrazide that confer a highly linear conformation to the polyacylhydrazone, making it more susceptible to crystallization.

We claim:
1. In a method of patterning a dielectric layer supported on a microelectronic substrate, where the method comprises ablating the dielectric layer by exposing the dielectric layer to laser energy so as to facilitate ablation of at least a portion of the dielectric layer, the improvement being that said dielectric layer is formed from a composition comprising a polymer selected from the group consisting of polyureas, polyurethanes, and polyacylhydrazones.
2. The method of claim 1, wherein said polymer is comprises recurring diisocyanate monomers and monomers selected from the group consisting of amine-terminated sulfones, hydroxyl-terminated sulfones, and mixtures thereof.
3. The method of claim 1, wherein said polymer comprises recurring dihydrazide monomers and recurring 2-hydroxyalkyl-linked dialdehyde monomers.
4. The method of claim 1, further comprising at least one intervening layer between said dielectric layer and said substrate.
5. The method of claim 1, wherein said composition comprises a polymer dissolved or dispersed in a solvent system, and said dielectric layer is formed by applying said composition to said microelectronic substrate, or to an intervening layer on said microelectronic substrate, and heating said composition at a temperature of from about 50° C. to about 250° C. for a time period of from about 5 minutes to about 30 minutes.
6. The method of claim 1, wherein said dielectric layer is exposed to laser energy at a wavelength of from about 100 nm to about 850 nm and at a pulse rate of from about 1 Hz to about 4,000 Hz.

7. The method of claim 1, wherein said ablation yields a pattern in said dielectric layer.

8. The method of claim 7, wherein said pattern includes openings selected from the group consisting of lines, spaces, and vias.

9. The method of claim 8, wherein said lines and spaces have a width of less than about 200 microns.

10. The method of claim 8, wherein said vias have a diameter of less than about 700 microns.

11. The method of claim 1, wherein said microelectronic substrate is selected from the group consisting of silicon, SiGe, $SiO_2$, $Si_3N_4$, SiON, aluminum, tungsten, tungsten silicide, gallium arsenide, germanium, tantalum, tantalum nitride, $Ti_3N_4$, hafnium, $HfO_2$, ruthenium, indium phosphide, coral, black diamond, and glass substrates.

12. The method of claim 1, wherein said dielectric layer has a thickness and wherein said ablation creates an opening in said dielectric layer that does not extend across its entire thickness.

13. A method of forming a polyacylhydrazone, said method comprising reacting a dihydrazide with a 2-hydroxyalkyl-linked dialdehyde to form said polyacylhydrazone, wherein the alkyl of the 2-hydroxyalkyl-linked dialdehyde has an odd number of carbon atoms.

14. The method of claim 13, wherein said polyacylhydrazone has a solubility of at least about 10% by weight in a polar, aprotic solvent.

15. The method of claim 13, wherein said dihydrazide is selected from the group consisting of adipic acid dihydrazide, isophthalic acid dihydrazide, and combinations thereof.

16. The method of claim 13, wherein said 2-hydroxyalkyl-linked dialdehyde is a 2-hydroxypropyl-linked dialdehyde.

17. The method of claim 13, wherein said 2-hydroxyalkyl-linked dialdehyde is a 2-hydroxyalkyl-linked aromatic dialdehyde.

18. The method of claim 13, said reaction being carried out in a solvent selected from the group consisting of dimethyl sulfoxide, N,N-dimethylformamide, N,N-dimethylacetamide, N-methylpyrrolidinone, and mixtures thereof, and in the presence of less than about 0.001% by weight catalyst, based upon the combined weight of dihydrazide and 2-hydroxypropyl-linked dialdehyde taken as 100% by weight.

* * * * *